United States Patent
Yanofsky et al.

(10) Patent No.: US 7,135,621 B2
(45) Date of Patent: *Nov. 14, 2006

(54) **CONTROL OF FRUIT DEHISCENCE IN PLANTS BY *INDEHISCENT1* GENES**

(75) Inventors: Martin F. Yanofsky, San Diego, CA (US); Sarah Liljegren, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/871,651

(22) Filed: Jun. 18, 2004

(65) Prior Publication Data
US 2005/0120417 A1 Jun. 2, 2005

Related U.S. Application Data

(63) Continuation-in-part of application No. 09/548,971, filed on Apr. 13, 2000, which is a continuation-in-part of application No. 09/339,998, filed on Jun. 25, 1999, now Pat. No. 6,410,826.

(60) Provisional application No. 60/090,649, filed on Jun. 25, 1998.

(51) Int. Cl.
*C12N 15/82* (2006.01)
*A01H 5/00* (2006.01)

(52) U.S. Cl. .................. 800/290; 435/320.1; 800/278; 800/298; 800/306

(58) Field of Classification Search ................ 800/290, 800/306, 278, 286, 276; 435/320.1
See application file for complete search history.

(56) References Cited

U.S. PATENT DOCUMENTS 6,998,517 B1 * 2/2006 Liljegren et al. ........... 800/290

OTHER PUBLICATIONS

Quattrocchio et al 1998, The Plant Journal 13(4): 475-488.*
Colliver et al 1997, Plant Molecular Biology 35:509-522.*

* cited by examiner

*Primary Examiner*—David H Kruse
(74) *Attorney, Agent, or Firm*—Townsend and Townsend and Crew LLP

(57) ABSTRACT

The present application provides methods and compositions that modulate fruit dehiscence in plants.

28 Claims, 3 Drawing Sheets

Figure 2

(sequence alignment of IND coding/rescue, bind2 put cDNA, and Bind 1 put cDNA)

SEQUENCE LISTING

```
<160> NUMBER OF SEQ ID NOS: 28

<210> SEQ ID NO 1
<211> LENGTH: 3856
<212> TYPE: DNA
<213> ORGANISM: Arabidopsis sp.
<220> FEATURE:
<223> OTHER INFORMATION: INDEHISCENT1 (IND1) genomic sequence, basic
      helix-loop-helix (bHLH) transcription factor
<220> FEATURE:
<221> NAME/KEY: CDS
<222> LOCATION: (2765)..(3361)
<223> OTHER INFORMATION: IND1

<400> SEQUENCE: 1
ctctagacca tctactatcc ggttgttgac ccttaaagct tttgaagact actagaataa      60
tgcaaatacc atatgtccat atccatcctt ttcttttgtt tgaactgaac attctaattt     120
tgtaaaagaa aaaaccttat gttaatatca ccgtaggcaa aaaaaatatc tcatcatatt     180
aaatttttat tataagatta tacattctct cgttgtaaga gttactccaa ttgcaagtgt     240
tgtattaact aataaaaagg acgaaagtag gaagcttata attaattgat gttgcatagt     300
actggtatat tgttgatgaa tataacaagt atgaacatta atgcatgaaa cggggtattt     360
tgtcttgaac tcattaaagg caatgtgaaa agaagatgtg aggtctcatt ttgaaaattt     420
atcttctagc tttgtcgatt ttaaatctat gaaatgaacg caacatatag aaatttcatg     480
tggacaacga catttagacg gtatcttaat tagaccgatt aattagtaat atacttatat     540 ataataattag tggtgattat aagtttactt atccacttga gaatttaaac aatgggcaat    600
accttaatgt cgaaagaagc cgtccccact tcgtgtaatg agttatgggg gagagatcct     660
gttaaatcgt caaataaaac aacttaagaa ctagaaattg acaccaaaaa tcataaagag     720
aacgttgaag aagtcattta tcgtatccag ctcatatttc ctagctaaga tcaaatcaag     780
gccgttgaaa gggcttgtaa gaaaatgtcg aagaaaccgt ggggtttaga agaaagacaa     840
gaaatagaag aacaatgatg ttaaattgcc tattttggtg tataggagtt gtcaaaagag     900
gagagagaga agaaaattag gtcaaaataa tgagcactaa aaatggagac atgtgttgag     960
taactattac aagagcgact tatgcttcct tatggcaatg atatccaaac caagtgcaa    1020 cgctcctttt ttgccctaat ttcgtaaagt ctctctcctt cttcgtcctt aggaaaaacc    1080
ctagaaattt aatcccttgt tcttgatctt gcttttgag taaccatgat tttgaccaca     1140
cactatttct tctatctttt gtggtctata ggattttgct ttatatgtgt ttcttgtatt    1200
```

-continued

```
gctccgtacg tacgtatacg aatttaaatg gttataacaa ggtttatata aactagcaca    1260
aatgagtcca tgaaatttgt tagcgaaaaa ggtagaaata tattgagtct ttaaacggca    1320
atatatataa ttttgctgca aaacttagct ttaatcatga tctaatgata ttttctttaa    1380
tttcctttgc caaattaatc acatgcacgg attttttggca agttatgtgt cgaattcttc    1440
cattcacaca acactaaact taattagaac tctaggaaat attttaaaat gacaacttta    1500
tcgaaaaaaa tttagttatg aaacaattc cagaattaaa catgagctat ataatttaag    1560
ataaaatgaa gtaatattga tatgtatgta ataacatatc tgattgcggt aaaaaaaaac    1620
atatctgatt aaattgttca tgcaggccca tgtcactatg atgtcatcac gtttttattt    1680
tcacaataac taatatatat tcaaaaaaat agttttgtca gattaaattt tttttggtgg    1740
tcagctttct ccaacctact aaactagttt ggaatgttct cttctttatt tttcttttc    1800 ttgatttctt atgttttta tttatggaat tttaagacgg attgtttagg tcgtttctct    1860
cttttcttgt tttctaaagt tacttttgta aactcatctc ctcccaatta gacagtcaat    1920
catatagtta tcttttaata tatgtctagt tgataaaaaa aatgaaaaaa tactggtggt    1980
agttctacta atgtttgtgt aaaaaatctg atattatgaa tctaatcaat ttctttgatc    2040
gtataatgtg ggttaaattt agtaattttt tacataaata agaactgtaa tgttgatgta    2100
tattggggaa tcagtatatt agcttgggta actatacttc tggaaatact tgaagattta    2160
actatttgca aaattataat ttagtcccga aaaatacaga cgacgggaca cgacaacata    2220
taagcaggtt tgaatcttgg aaaattttgt atacataacc tatataaata ctaatgttct    2280
ggttgggttc aaaagccttt tcaaaagttc cattttttaa attcaaggac attttacata    2340
ggaaataagt tgagtcataa aaaataatgg ttattttgta aggttttttt tttgattaaa    2400
acgcacatat taagaagtta gtttttttc actaccaaat atcaattaat ttaaaaccat    2460
gcaaccattc ataaaacaat actattaaag aatataaata atcacaaaat attaaataca    2520
cttaaaattt acatataaat ttacaaaaca tctaattaat tgaaacagaa aggaaaaggt    2580
aaaatatatc ataaaatgag acatatatcc tataaaaaaa aaatgaggca tatgaagtaa    2640
ataataagag acatgcatgt aagcattcgg ttaattaatc gagtcaaaga tatatatcag    2700
taaaatcata tgtgtatatt tctgaaaaaa gaatatatat attgagaaat aagaaaagat    2760 gaaa atg gaa aat ggt atg tat aaa aag aaa gga gtg tgc gac tct tgt    2809
     Met Glu Asn Gly Met Tyr Lys Lys Lys Gly Val Cys Asp Ser Cys
     1               5                   10                  15 gtc tcg tcc aaa agc aga tcc aac cac agc ccc aaa aga agc atg atg    2857
Val Ser Ser Lys Ser Arg Ser Asn His Ser Pro Lys Arg Ser Met Met
                20                  25                  30 gag cct cag cct cac cat ctc ctc atg gat tgg aac aaa gct aat gat    2905
Glu Pro Gln Pro His His Leu Leu Met Asp Trp Asn Lys Ala Asn Asp
            35                  40                  45 ctt ctc aca caa gaa cac gca gct ttt ctc aat gat cct cac cat ctc    2953
Leu Leu Thr Gln Glu His Ala Ala Phe Leu Asn Asp Pro His His Leu
        50                  55                  60 atg tta gat cca cct ccc gaa acc cta att cac ttg gac gaa gac gaa    3001
Met Leu Asp Pro Pro Pro Glu Thr Leu Ile His Leu Asp Glu Asp Glu
    65                  70                  75 gag tac gat gaa gac atg gat gcg atg aag gag atg cag tac atg atc    3049
Glu Tyr Asp Glu Asp Met Asp Ala Met Lys Glu Met Gln Tyr Met Ile
80                  85                  90                  95 gcc gtc atg cag ccc gta gac atc gac cct gcc acg gtc cct aag ccg    3097
Ala Val Met Gln Pro Val Asp Ile Asp Pro Ala Thr Val Pro Lys Pro
```

```
aac cgc cgt aac gta agg ata agc gac gat cct cag acg gtg gtt gct    3145
Asn Arg Arg Asn Val Arg Ile Ser Asp Asp Pro Gln Thr Val Val Ala
            115                 120                 125 cgt cgg cgt cgg gaa agg atc agc gag aag atc cga att ctc aag agg    3193
Arg Arg Arg Arg Glu Arg Ile Ser Glu Lys Ile Arg Ile Leu Lys Arg
        130                 135                 140 atc gtg cct ggt ggt gcg aag atg gac aca gct tcc atg ctc gac gaa    3241
Ile Val Pro Gly Gly Ala Lys Met Asp Thr Ala Ser Met Leu Asp Glu
145                 150                 155 gcc ata cgt tac acc aag ttc ttg aaa cgg cag gtg agg att ctt cag    3289
Ala Ile Arg Tyr Thr Lys Phe Leu Lys Arg Gln Val Arg Ile Leu Gln
    160                 165                 170                 175 cct cac tct cag att gga gct cct atg gct aac ccc tct tac ctt tgt    3337
Pro His Ser Gln Ile Gly Ala Pro Met Ala Asn Pro Ser Tyr Leu Cys
                180                 185                 190 tat tac cac aac tcc caa ccc tga tgaactacac agaagctcgc tagctagaca   3391
Tyr Tyr His Asn Ser Gln Pro
                195 tttggtgtca tcctctcaac cttttttcatg ttgatatatt atatatagat gcataaagat  3451 tcgatccaag attgtatggg tgttttaata ttattattct aagatatatg atgtacaatt   3511 gtgtaccaag tttctttatc ttgatatcat atgcataaat aattggtgaa taaaaagaag   3571 atattgattg taaacaaaaa aaagaagata ttgattgtta attagggttt gatcattctg   3631 tatgaaagct ttggcctgca aattaatttt cgatatatat atatatatat ggagaatata   3691 tatcaaatac tttttaattt tgactataat ttgtatcaat tatctgaatc tgatgagtgt   3751 aggttatata tggattagca aaaaagaaaa caaccattat tacgcaccta cattaaaaat   3811 catccaccaa agaagaaacc atcctcaaga gggttccctc tagag                  3856
```

<210> SEQ ID NO 2
<211> LENGTH: 198
<212> TYPE: PRT
<213> ORGANISM: Arabidopsis sp.
<220> FEATURE:
<223> OTHER INFORMATION: INDEHISCENT1 (IND1), basic helix-loop-helix
      (bHLH) transcription factor

<400> SEQUENCE: 2

```
Met Glu Asn Gly Met Tyr Lys Lys Lys Gly Val Cys Asp Ser Cys Val
1               5                   10                  15

Ser Ser Lys Ser Arg Ser Asn His Ser Pro Lys Arg Ser Met Met Glu
            20                  25                  30

Pro Gln Pro His His Leu Leu Met Asp Trp Asn Lys Ala Asn Asp Leu
        35                  40                  45

Leu Thr Gln Glu His Ala Ala Phe Leu Asn Asp Pro His His Leu Met
    50                  55                  60

Leu Asp Pro Pro Glu Thr Leu Ile His Leu Asp Glu Asp Glu Glu
65                  70                  75                  80

Tyr Asp Glu Asp Met Asp Ala Met Lys Glu Met Gln Tyr Met Ile Ala
                85                  90                  95

Val Met Gln Pro Val Asp Ile Asp Pro Ala Thr Val Pro Lys Pro Asn
            100                 105                 110

Arg Arg Asn Val Arg Ile Ser Asp Asp Pro Gln Thr Val Val Ala Arg
        115                 120                 125

Arg Arg Arg Glu Arg Ile Ser Glu Lys Ile Arg Ile Leu Lys Arg Ile
    130                 135                 140
```

```
Val Pro Gly Gly Ala Lys Met Asp Thr Ala Ser Met Leu Asp Glu Ala
145                 150                 155                 160

Ile Arg Tyr Thr Lys Phe Leu Lys Arg Gln Val Arg Ile Leu Gln Pro
            165                 170                 175

His Ser Gln Ile Gly Ala Pro Met Ala Asn Pro Ser Tyr Leu Cys Tyr
        180                 185                 190

Tyr His Asn Ser Gln Pro
        195

<210> SEQ ID NO 3
<211> LENGTH: 2765
<212> TYPE: DNA
<213> ORGANISM: Arabidopsis sp.
<220> FEATURE:
<221> NAME/KEY: promoter
<222> LOCATION: (1)..(2765)
<223> OTHER INFORMATION: IND1 5' promoter

<400> SEQUENCE: 3
ctctagacca tctactatcc ggttgttgac ccttaaagct tttgaagact actagaataa      60
tgcaaatacc atatgtccat atccatcctt ttcttttgtt tgaactgaac attctaatttt    120 tgtaaaagaa aaaaccttat gttaatatca ccgtaggcaa aaaaaatatc tcatcatatt    180
aaatttttat tataagatta tacattctct cgttgtaaga gttactccaa ttgcaagtgt     240
tgtattaact aataaaaagg acgaaagtag gaagcttata attaattgat gttgcatagt    300
actggtatat tgttgatgaa tataacaagt atgaacatta atgcatgaaa cggggtattt     360
tgtcttgaac tcattaaagg caatgtgaaa agaagatgtg aggtctcatt ttgaaaattt    420
atcttctagc tttgtcgatt ttaaatctat gaaatgaacg caacatatag aaatttcatg    480
tggacaacga catttagacg gtatcttaat tagaccgatt aattagtaat atacttatat    540
atataattag tggtgattat aagtttactt atccacttga gaatttaaac aatgggcaat    600
accttaatgt cgaaagaagc cgtccccact tcgtgtaatg agttatgggg gagagatcct    660
gttaaatcgt caaataaaac aacttaagaa ctagaaattg acaccaaaaa tcataaagag    720
aacgttgaag aagtcattta tcgtatccag ctcatatttc ctagctaaga tcaaatcaag    780
gccgttgaaa gggcttgtaa gaaaatgtcg aagaaaccgt ggggtttaga agaaagacaa    840
gaaatagaag aacaatgatg ttaaattgcc tattttggtg tataggagtt gtcaaaagag    900
gagagagaga agaaaattag gtcaaaataa tgagcactaa aaatggagac atgtgttgag    960
taactattac aagagcgact tatgcttcct tatggcaatg atatccaaac caaagtgcaa   1020
cgctcctttt ttgccctaat ttcgtaaagt ctctctcctt cttcgtcctt aggaaaaacc   1080
ctagaaattt aatcccttgt tcttgatctt gcttttgag taaccatgat tttgaccaca    1140
cactatttct tctatctttt gtggtctata ggattttgct ttatatgtgt ttcttgtatt    1200
gctccgtacg tacgtatacg aatttaaatg gttataacaa ggtttatata aactagcaca   1260
aatgagtcca tgaaatttgt tagcgaaaaa ggtagaaata tattgagtct ttaaacggca    1320
atatatataa ttttgctgca aaacttagct ttaatcatga tctaatgata ttttctttaa   1380
tttcctttgc caaattaatc acatgcacgg attttttggca agttatgtgt cgaattcttc   1440
cattcacaca acactaaact taattagaac tctaggaaat attttaaaat gacaacttta   1500
tcgaaaaaaa tttagttatg aaaacaattc cagaattaaa catgagctat ataatttaag   1560
ataaaatgaa gtaatattga tatgtatgta ataacatatc tgattgcggt aaaaaaaaac   1620
```

-continued

```
atatctgatt aaattgttca tgcaggccca tgtcactatg atgtcatcac gtttttattt      1680
tcacaataac taatatatat tcaaaaaaat agttttgtca gattaaattt ttttttggtgg     1740 tcagctttct ccaacctact aaactagttt ggaatgttct cttctttatt tttcttttc      1800 ttgatttctt atgtttttta tttatggaat tttaagacgg attgtttagg tcgtttctct     1860
cttttcttgt tttctaaagt tacttttgta aactcatctc ctcccaatta gacagtcaat     1920
catatagtta tcttttaata tatgtctagt tgataaaaaa aatgaaaaaa tactggtggt     1980
agttctacta atgtttgtgt aaaaaatctg atattatgaa tctaatcaat ttctttgatc     2040
gtataatgtg ggttaaattt agtaatttt tacataaata agaactgtaa tgttgatgta     2100
tattggggaa tcagtatatt agcttggta actatacttc tggaaatact tgaagattta     2160
actatttgca aaattataat ttagtcccga aaaatacaga cgacgggaca cgacaacata    2220
taagcaggtt tgaatcttgg aaaattttgt atacataacc tatataaata ctaatgttct    2280
ggttgggttc aaaagccttt tcaaaagttc cattttttaa attcaaggac attttacata    2340
ggaaataagt tgagtcataa aaaataatgg ttattttgta aggttttttt tttgattaaa    2400
acgcacatat taagaagtta gttttttttc actaccaaat atcaattaat ttaaaaccat    2460
gcaaccattc ataaaacaat actattaaag aatataaata atcacaaaat attaaataca    2520
cttaaaattt acatataaat ttacaaaaca tctaattaat tgaaacagaa aggaaaaggt    2580
aaaatatatc ataaaatgag acatatatcc tataaaaaaa aaatgaggca tatgaagtaa    2640
ataataagag acatgcatgt aagcattcgg ttaattaatc gagtcaaaga tatatatcag    2700
taaatacata tgtgtatatt tctggaaaaa gaatatatat attgagaaat aagaaaagat    2760
gaaaa                                                                 2765
```

<210> SEQ ID NO 4
<211> LENGTH: 496
<212> TYPE: DNA
<213> ORGANISM: Arabidopsis sp.
<220> FEATURE:
<221> NAME/KEY: 3'UTR
<222> LOCATION: (1)..(496)
<223> OTHER INFORMATION: IND1 3' untranslated sequence

<400> SEQUENCE: 4

```
atgaactaca cagaagctcg ctagctagac atttggtgtc atcctctcaa ccttttcat       60 gttgatatat tatatataga tgcataaaga ttcgatccaa gattgtatgg gtgttttaat     120
attattattc taagatatat gatgtacaat tgtgtaccaa gtttctttat cttgatatca     180
tatgcataaa taattggtga ataaaaagaa gatattgatt gtaaacaaaa aaaagaagat     240
attgattgtt aattagggtt tgatcattct gtatgaaagc tttggcctgc aaattaattt     300
tcgatatata tatatatata tggagaatat atatcaaata cttttttaat ttgactataa    360
tttgtatcaa ttatctgaat ctgatgagtg taggttatat atggattagc aaaaaagaaa    420
acaaccatta ttacgcacct acattaaaaa tcatccacca aagaagaaac catcctcaag    480
agggttccct ctagag                                                     496
```

<210> SEQ ID NO 5
<211> LENGTH: 5622
<212> TYPE: DNA
<213> ORGANISM: Arabidopsis sp.
<220> FEATURE:
<223> OTHER INFORMATION: SHATTERPROOF1 (SHP1) genomic sequence
<220> FEATURE:
<221> NAME/KEY: modified_base
<222> LOCATION: (935)..(941)
<223> OTHER INFORMATION: n = g, a, c or t

<400> SEQUENCE: 5

| | | | | | |
|---|---|---|---|---|---|
| agatctgcaa | cagtgaaaag | agaaaacaaa | atggacttga | agaggttttg | acaatgccag | 60 |
| agataatgct | tattccctaa | tatgttgcca | gccaagtgtc | aaattggctt | tttaaatatg | 120 |
| gatttctgta | tcagtggtca | tatttgtgga | tccaacgtat | tcatcatcaa | gttctcaagt | 180 |
| ttgctttcag | tgcaattcta | attcacacgt | ttaactttaa | catgcatgtc | attataatta | 240 |
| cttcttcact | aagacacaat | acggcaaacc | tttcagatta | tattaatctc | cataaatgaa | 300 |
| ataattaacc | tcataatcaa | gattcaatgt | ttctaaatat | atatggacaa | aatttacacg | 360 |
| gaagattaga | tacgtatatt | agtagattta | gtctttcgtt | tgtgcgataa | gattaaccac | 420 |
| ctcatagata | gtaatatcat | tgtcaaattc | ctctcggttt | agtcgctaaa | ttgtatcttt | 480 |
| tttaagccta | aaagtagtgt | attcgcatat | gacttatcgt | cctaactttt | tttttaatta | 540 |
| acaaaaaaat | cgaaagaaaa | ataatctgtt | aaatattttt | taagtactcc | attaagttta | 600 |
| gtttctattt | aaaaaatgct | tgaaatttga | cagttatgtt | caacaatttt | gaatcatgag | 660 |
| cgatgtctag | atactcagaa | tttaatcaag | atgtcttatc | aaatttgttg | tcactcgagg | 720 |
| acccacgcaa | aagaaaagac | taatatgatt | tttatttggt | ctggatattt | ttgtagagga | 780 |
| tgaaactaag | agagtgaaag | attcgaaatc | cacaatgttc | aagagagctc | aaagcaaaaa | 840 |
| gaaaatgaa | gatgaaggac | taaagaacaa | taagcaacta | cttataccct | atttccataa | 900 |
| aggattcagg | tactaggaga | agttgaggca | agttnnnnnn | nattgattca | aatttttcatt | 960 |
| tattttttaca | atttaattca | cctaagttat | tatgcatttc | tcatcattgg | tacattttct | 1020 |
| gtatagcgta | tttacatata | tgaaataaat | taaatatgtc | ctcacgttgc | aagtagttaa | 1080 |
| tgaatgtccc | cacgcaaaaa | aaatccctc | caaatatgtc | cacctttct | tttcttttta | 1140 |
| attccaaaat | taccataaac | ttttggttta | caaaagattt | ctagaaattg | aggaagatat | 1200 |
| cctaaatgat | tcatgaatcc | ttcaataatc | tgaagtttgc | gatattttcg | attttcttca | 1260 |
| agagttgcga | tatttgtaat | ttggtgacct | taaactttt | ttgataaaga | gtaaacgttt | 1320 |
| tttcttaaaa | gtaaaacttg | attttatgtt | ttagggttct | agctcaactt | tgtattatat | 1380 |
| ttcttgcaaa | aagagttcgt | taactgcatt | cttcaacact | ataaagtgat | tatcaaaaac | 1440 |
| atcttcatga | acattaagaa | aaacaatatt | tggtttcggt | tagagcttgg | ttttgcttgg | 1500 |
| cttgattcac | atacccattc | tagactttgg | cataaatttg | atacgataga | gagtatctaa | 1560 |
| tggtaatgca | gaagggtaaa | aaaaggaaga | gagaaaaggt | gagaaagatt | accaaaaata | 1620 |
| aggagtttca | aaagatggtt | ctgatgagaa | acagagccca | tccctctcct | tttcccttc | 1680 |
| ccatgaaaga | aatcggatgg | tcctccttca | atgtcctcca | cctactcttc | tcttctttct | 1740 |
| tttttttcttt | cttattatta | accatttaat | taatttcccc | ttcaatttca | gtttctagtt | 1800 |
| ctgtaaaaag | aaaatacaca | tctcacttat | agatatccat | atctatttat | atgcatgtat | 1860 |
| agagaataaa | aaagtgtgag | tttctaggta | tgttgagtat | gtgctgtttg | gacaattgtt | 1920 |
| agatgatctg | tccattttttt | tcttttttct | tctgtgtata | aatatatttg | agcacaaaga | 1980 |
| aaaactaata | accttctgtt | ttcagcaact | agggtcttat | aaccttcaaa | gaaatattcc | 2040 |
| ttcaattgaa | aacccataaa | ccaaaataga | tattacaaaa | ggaaagagag | atattttcaa | 2100 |
| gaacaacata | attagaaaag | cagaagcagc | agtaagtgg | tactgagata | aatgatatag | 2160 |
| tttctcttca | agaacagttt | ctcattaccc | accttctcct | ttttgctgat | ctatcgtaat | 2220 |

-continued

```
cttgagaact caggtaaggt tgtgaatatt atgcaccatt cattaaccct aaaaataaga     2280
gatttaaaat aaatgtttct tctttctctg attcttgtgt aaccaattca tgggtttgat     2340
atgtttcttg gttattgctt atcaacaaag agatttgatc attataaagt agattaataa     2400
ctcttaaaca cacaaagttt ctttatttt tagttacatc cctaattcta gaccagaaca      2460
tggatttgat ctatttcttg gttatgtatc ttgatcagga aaagggattt gatcatcaag     2520
attagccttc tctctctctc tctagatatc tttcttgaat ttagaaatct ttatttaatt    2580
atttggtgat gtcatatatg gatcaatgga ggaaggtggg agtagtcacg acgcagagag    2640
tagcaagaaa ctagggagag ggaaaataga gataaagagg atagagaaca caacaaatcg    2700
tcaagttact ttctgcaaac gacgcaatgg tcttctcaag aaagcttatg aactctctgt    2760
cttgtgtgat gccgaagttg ccctcgtcat cttctccact cgtggccgtc tctatgagta    2820
cgccaacaac aggtacgctt ctcctactct atttcttgat cttgttttct taattttaac    2880
taaacaagat cctagttcaa atgataacaa agtggggatt gagagccaag attagggttt    2940
ggttaattta gaaaaccaga tttcacttgt tgatacattt aatatctctc tagctagatt    3000
tagtactctc tcctctatat atgtgtgggt gtgtgtgtaa gtgtgtatat gtatgcaaat    3060
gcaagaagaa gaagaaaaag ttatcttgtc ttctcaaatt ctgatcagct ttgaccttag    3120
tttcactctt ttttctgcaa atcatttgaa cctgatgcat gtcagtttct acaatacact    3180
tttaattttg acggcccatc aaatttccta gggtttactt cagtgaacaa aattgggttc    3240
ttgacacgat ttagcatgta tatataaaaa taggggatga tcaagactta tgtaacctct    3300
gtctggtgaa actagggaca aagtctactg atgagttgtc actagggatc catttgatca    3360
tttaatccca acaaaaatga aacaaatttt tgagaattta tatgctgaag tttttcaacc    3420
ctctttttta aataacttta tattatgtag atttgtattt agggtaattt gtccaactag    3480
aagtcctaaa atcaataaa cacacggatg actttgtcta acattgtatc agtcatcaaa     3540
tgtaaaattg tacaaataat gaaattaaag atttagtctc tttattttt tttgtttagg     3600 gtgtatatat atatatatat gtatatttgt tgcattgata tatcaatgag agggagagaa    3660
ctcagagaag tgtcggaaat taaaatggta cgagccaatt ggaatctctg gcattctgag    3720
cttcatttgt ttgttattag aaaaaaaaaa aaaaatcct ttaaagatac cttcatgatg     3780
acattgaatc atgtaatata cacgatacat ggtctaattc ctcctcaaac cctaattacc    3840
aatttcgaaa ccataatatt tactagtatg tttatatatc cttactttaa gacattgttt    3900
gtttataata ccttgtgaat taagaaaaaa aaaaaaaaac ttgtggatct attcaagcca    3960
tgtgttagaa taaatttata aattttctcc tcgtactggt cagatattgg tccaaactcc    4020
aaagccttcc cttttcagga aaaaaacat ttcgaaatta actctaatta atcaagaatt     4080
tcctacaatg tatacatcta atgttttttc cgcgatctta cttattagtg tgagggtac     4140 aattgaaagg tacaagaaag cttgttccga tgccgtcaac cctccttccg tcaccgaagc    4200
taatactcag gtaccaattt atattgtttg attctctttg ttttatcttc ttcttttcat    4260
tatatatatg atcaacaaaa aatataacct acaaaagag agagttcaag gaaatgcatt     4320
gaaacggttt cgttatggtg tttgaataca tggattttg aagtactatc agcaagaagc     4380
ctctaagctt cggaggcaga ttcgagatat tcagaattca aataggtaat tcattaactt    4440
ttcatgaact cttcgatttg gtattaggtc acttaatttg gtgtcggtcc aaaagtccgc    4500
ttgtagtttt ctttagaagt tgttttgttt aatgttcatg tttacaaatt gaaggcatat    4560
tgttggggaa tcacttggtt ccttgaactt caaggaactc aaaaacctag aaggacgtct    4620
```

| | |
|---|---|
| tgaaaaagga atcagccgtg tccgctccaa aaggtaaaa tctacgttgc tctctctctg | 4680 |
| tgtctctgtc tctctctcta tatatagtcc cttagtttat atagttcatc accctttttgt | 4740 |
| gagaattttg cagaatgagc tgttagtggc agagatagag tatatgcaga agagggtaag | 4800 |
| aacgtttctc ccattccaag taattagatc tttcttcgtc tttgtgaggg tttgagtttt | 4860 |
| cccataaatc atgtgtagga aatggagttg caacacaata acatgtacct gcgagcaaag | 4920 |
| gttagccacg ttctgttcca aatcttaatc tcaatatcta ctcttttctt cattgtataa | 4980 |
| ctaagataac gtgaataaca agaaaacttt tgttttttggg tttaatagat agccgaaggc | 5040 |
| gccagattga atccggacca gcaggaatcg agtgtgatac aagggacgac agtttacgaa | 5100 |
| tccggtgtat cttctcatga ccagtcgcag cattataatc ggaactatat tccggtgaac | 5160 |
| cttcttgaac cgaatcagca attctccggc caagaccaac ctcctcttca acttgtgtaa | 5220 |
| ctcaaaacat gataacttgt ttcttcccct cataacgatt aagagagaga cgagagagtt | 5280 |
| cattttatat ttataacgcg actgtgtatt catagtttag gttctaataa tgataataac | 5340 |
| aaaactgttg tttctttgct taattacatc aacatttaaa tccaaagttc taaaacacgt | 5400 |
| cgagatccaa agtttgtcat acaagattag acgcatacac gatcagttaa tagattttaa | 5460 |
| gtgccttta atatttacat atagttgcag cttcgattag atcatgtcca ccaaacactc | 5520 |
| acaattagag acaagcaaaa ctataaacat tgatcataaa atgattacaa catgtccata | 5580 |
| aattaattat ggattacaaa ataaaaaact tacaaaagat ct | 5622 |

<210> SEQ ID NO 6
<211> LENGTH: 6138
<212> TYPE: DNA
<213> ORGANISM: Arabidopsis sp.
<220> FEATURE:
<223> OTHER INFORMATION: SHATTERPROOF2 (SHP2) genomic sequence

<400> SEQUENCE: 6

| | |
|---|---|
| gaattcgtaa cagaatttag tgaataatat tgtaattacc aggcaaggac tctccaaacg | 60 |
| gatagctcga atatcgttat taagagtaa atgatccaat atgtaagcca ttgttgatca | 120 |
| tctaacattg ttggactctc tattgctcga aatgatgcat acctaatcat ttattcagtt | 180 |
| aactatcaag ttgcatttgt aaaaccaaa catttaaatt cagatttgat atcacttaca | 240 |
| gaggatagag aagcatgact ccaggcctgc atgcaacaag aaaaaggaag aaaataatgt | 300 |
| taaaaatttg acaatatag tgtttatttt tattatatga gacagaattt gaataaaatc | 360 |
| ctacccaact agagcatcaa aacgttttgc aatcgcaata atgaaaccca ttttcttttt | 420 |
| gagttttac tcttctttca acagaaactt tctcaaacgt ctttagcact gtgacgttag | 480 |
| atatatacac aaaagcttga aatttcttca agcaaaagaa tctttgtggg agttaaggca | 540 |
| acaagccagg taaagaatct ccaacgcatt gttacgtttt catgaaccta tttattatat | 600 |
| gttctaagaa agaaaaaaat atctcaaagt aaacgttgga aatttctga tgaagggaaa | 660 |
| tccaaagtct tgggtttagt atccctatga atggtatttg gaatatgttt tcgtcaaaac | 720 |
| aaaagattct ttctttttc acaagagtta gtgatcaata acttatgcac taattaatga | 780 |
| gattggacgt atacacaatt tgattatgat acttgagtaa aaatcacctg tcctttaatt | 840 |
| tggaaatctc tctttcttac ccatttatat actacttctt ttcattaaaa ttaaatttca | 900 |
| attatcaatc atcgttcaat ttgataaaga tttaacattt tttgtcacag ggctagtaaa | 960 |
| agcaatcttt acataattca tctttcttac atatatatat tacctttttc ttcattagta | 1020 |

```
ttctatttga ttatgattat tttgtcataa agctagtaaa ttaaacactc gatatgagaa    1080
ttatattact tcacgctaat taactcttaa cacaacaaga actagtgcat attcaacttt    1140
caaagcatat actatatatt gagaatatag accacgaaag tcaatcaaaa gacctaccag    1200
ctctcatcaa gttctttctt gaaatgattt tgcagaattt ccaacttaat taattcgaca    1260
tgaatgtgaa aatgtgtgtt gctcgttaag aaaattgaat agaagtacaa tgaaaatgat    1320
gaggaatggg caaaacacaa aagagtttcc tttcgtaact acaattaatt aatgcaaatc    1380
tgagaaaggg ttcatggata atgactacac acatgattag tcattccccg tgggctctct    1440
gctttcattt actttattag tttcatcttc tctaattata ttgtcgcata tatgatgcag    1500
ttcttttgtc taaattacgt aatatgatgt aattaattat caaataaaat attcaaattg    1560
ccgttggact aacctaatgt ccaagattaa gacttgaaca taagaatttt ggaaaaacta    1620
aaccagttat aatatatact cttaaattgc catttctgaa cacaaccaaa taataatata    1680
tactatttac agttttttt aattggcaag aacactgaaa tcttattcat tgtctcgctt    1740
ggtagttgac aagttataac actcatattc ataataaccccc attctaacgt tgacgacgaa    1800
cactcatata aaccacccaa attcttagca tattagctaa atattggttt aattggaaat    1860
atttttttta tatataaaat gccaggtaaa tattaacgac atgcaatgta tataggagta    1920
gggcaataaa aagaaaagga gaataaaaag ggattaccaa aaaaggaaag tttccaaaag    1980
gtgattctga tgagaaacag agcccatacc tctctttttt cctctaaaca tgaaagaaaa    2040
attggatggt cctccttcaa tgctctctcc ccacccaatc caaacccaac tgtcttcttt    2100
cttttctttt tcttctttct aatttgatat tttctaccac ttaattccaa tcaatttcaa    2160
atttcaatct aaatgtatgc atatagaatt taattaaaag aattaggtgt gtgatatttg    2220
agaaaatgtt agaagtaatg gtccatgttc tttctttctt tttccttcta taacacttca    2280
gtttgaaaaa aaactaccaa accttctgtt ttctgcaaat gggttttaa atacttccaa    2340 agaaatattc ctctaaaaga aattataaac caaaacagaa accaaaaaca aaaaataaag    2400
ttgaagcagc agtaagtgg tactgagata ataagaatag tatctttagg ccaatgaaca    2460
aattaactct ctcataattc atcttcccat cctcacttct ctttctttct gatataatta    2520
atcttgctaa gccaggtatg gttattgatg atttacactt tttttttaaaa gtttcttcct    2580 tttctccaat caaattcttc agttaatcct tataaaccat ttctttaatc caaggtgttt    2640
gagtgcaaaa ggatttgatc tatttctctt gtgtttatac ttcagctagg gcttatagaa    2700
atggagggtg gtgcgagtaa tgaagtagca gagagcagca agaagatagg gagagggaag    2760
atagagataa agaggataga gaacactacg aatcgtcaag tcactttctg caaacgacgc    2820
aatggtttac tcaagaaagc ttatgagctc tctgtcttgt gtgacgctga ggttgctctt    2880
gtcatcttct ccactcgagg ccgtctctac gagtacgcca acaacaggta cacatctttt    2940
agctagatct tgattttgtt gaatttttt tctagaataa agtttcgact cttctggtgg    3000 gttttttcaat ctttatggtc tctttatagt tttttttcctt agtttctctg aagctcaaat    3060
ctctttaaaa atccccaaaa ttagggtttg tttaaaacta gggaaccccta ctttaacttc    3120 tttctcttag taaaaaagca gtgagggtct tctctgatca ttaattagca tcccccatac    3180
cttgttccag tcacttttc tccacaaatc cttataacag tatctatata tgtatctatt    3240
tatgtcagtt tgtacaagac acttcgatca atttgatgac ccatcaagtt ttatttctgc    3300
agattgatca ttaggtttcc atcatagtaa tgaaaaagta gggttcttga taaaattata    3360
ataatatata ttatttggct atataaaaaa gctatgtaga ttccttaaaa attgattcac    3420
```

-continued

```
tagggagaga ctagtaggtg tttgtcttct gacacttctc taatcttttg gtgaatcctt     3480
ttgttaaatc aagaaaatga atcagggaca aagcttattg ttgagtcact taattaatca     3540
tccgatccat caatcaagaa aaataacgaa acagaaaatt ttgattttg attgttattt      3600 tctccacttc aagttgggga cttgtcattt ccgttttct atacgtttcc agctattaac      3660
agctcatgtt catttcacca ttttgattat ttgtctgctt tttaaagata aatgttttca     3720
aaaatattgt ttttatttgc ttggctagtt aatactataa ttgaggttga tgtatgacta     3780
taatctataa gtcaagtctc atatcatgga tctaagttaa aactagtaaa tttgtagttt     3840
caatgtgaac tttcacaacg actaaagaac tgatctgaag tttataatgg acatgactaa     3900
tttgattaac aaaagaggaa tgcattatgt atgtagaaac atgtgatata tatatgtttc     3960
tattatcaaa agtgtagtta actttcttat ttcaaacacc ctcatgcttt agtagtatct     4020
tacttttgac atttctcaac ttcagctttc cattatacaa cagcacaatg taaattactt     4080
gtatatgaat atgaaagcat aacgttatgc aaagatttct agcttttctt tttctgtttt     4140
gcaaaagatt tacaaatatc atgttcttgg taaaaacata cttgcctcag ccacatatgc     4200
atgtaaatgt aatgttcaaa tattaattca ggaaaaacaa agaagaagca aaattagctt     4260
ctagagtagg gaatctattg acttgacctg aaaatcactt cttttctta aagcctagta      4320 gtgaattttt taatctaatt aggccaaaat atatactagc ctaaaatata atttggattt     4380
tgtgtcgtac ataaattggg accaattcca attaactaag agcatatgca attcaaattc     4440 ttttttatttt cttctccgat ttgctacttc ttttcttttgt atgttttcaa attaggatta   4500
cacttttttg gggaagtaca cattagggtc ttctcgaact ttgattatac atatatatat     4560
atatatatat atataacttt gtgagatgtc actgttaata gataataggc aataacaata     4620
atatccaaaa aagaaggcgc aaacaaatca tatactatat ggtactggtc cattcactat     4680
tttgtcggtt gaatttaagg tttggcgtac aaactttgtt tcaaaccttt attattccgt     4740
ctttctgtgt gttttgtata tccagaagat aaaaatatca atttctttaa cgacttcata     4800
tatatatata tatatatata tatatatatt tttctcttct ggttttagtg tttgaatcca     4860
acagttatag tttcgtgtgt ctttgtttta cttgtggtgg tttaagtttg agattttcac     4920
cgattgcatc tatttacata tatagctacc acaaaaaaga ttgcatttta aaatcttttc     4980
ctttgtgtga atgttgatga agtgtgagag gaacaataga aaggtacaag aaagcttgct     5040
ccgacgccgt taaccctccg accatcaccg aagctaatac tcaggttagc ttttaattaa     5100
tacacctagc tagctagttc gttaattact taatttcttc ttcttttagt tatctgacct     5160
ttttttcacc tcttgtaaca atgatgggat cgaaattgat gaagtactat cagcaagagg     5220 cgtctaaaact ccggagacag attcgggaca ttcagaattt gaacagacac attcttggtg    5280
aatctcttgg ttccttgaac tttaaggaac tcaagaacct tgaaagtagg cttgagaaag     5340
gaatcagtcg tgtccgatcc aagaaggtac atcactaact ctccatcaat ctccttatca     5400
ttgaatatat atccatctga ttcttgcccg ttatatttgg ttttttctctc cagcacgaga    5460 tgttagttgc agagattgaa tacatgcaaa aaagggtaaa agtaaaacct atcttccttc     5520
acaatgaact acccctactt tattagcaac ttctctttct gatgatcatc ttttttattt     5580
tctgttgtcg cttgcattgt aggaaatcga gctgcaaaac gataacatgt atctccgctc     5640
caaggtttta tacataactc ttttttggcat ttttgatcat cattttttc cggtagacaa     5700 tctcttgatg tgcaaattct aaatatctct gcagattact gaaagaacag gtctacagca     5760
```

```
acaagaatcg agtgtgatac atcaagggac agtttacgag tcgggtgtta cttcttctca    5820
ccagtcgggg cagtataacc ggaattatat tgcggttaac cttcttgaac cgaatcagaa    5880
ttcctccaac caagaccaac cacctctgca acttgtttga ttcagtctaa cataagcttc    5940
tttcctcagc ctgagatcga tctatagtgt cacctaaatg cggccgcgtc cctcaacatc    6000
tagtcgcaag ctgaggggaa ccactagtgt catacgaacc tccaagagac ggttacacaa    6060
acgggtacat tgttgatgtc atgtatgaca atcgcccaag taagtatcca gctgtgttca    6120
gaacgtacgt ccgaattc                                                  6138
```

```
<210> SEQ ID NO 7
<211> LENGTH: 633
<212> TYPE: DNA
<213> ORGANISM: Brassica napus
<220> FEATURE:
<223> OTHER INFORMATION: Bn INDEHISCENT1 (IND1) putative cDNA

<400> SEQUENCE: 7
atgtataaaa gaaaggtcta tgcgtctcta gtccaaaaac tctatatgtc tggttcaaaa     60
gcagatgcag cagccatagc cccaatagtc atgatggagc tcatcatct ccttatgaac    120 tggaacaaac ctattgatct cattacacaa gaaaactctt ttaaccacaa tcctcatttc    180
atggtagatc caccttccga aaccctaagc cacttccagc cccgccgac agtcttctcc    240 gatcccggag gaggagagga agcagaagac gaagaaggag aggaagagat agatgagatg    300
aaggagatgc aatacgcgat tgctgccatg cagcccgtag acatcgatcc agccaccgtt    360
cctaagccga accgccgtaa cgtaagggta agcgaggacc cccagacggt ggtggctcgt    420
cggcgtagag aaaggataag cgagaagatc cggatattga agaggatggt gccaggcggt    480
gcaaagatgg acactgcctc catgcttgac gaagccatcc gctacaccaa gttcttgaaa    540
cggcaggtga ggcttcttca gcctcacact cagcttgggg ctcctatgtc tgaccttct    600 cgcctttgtt attaccacaa ctcggatacc taa                                 633
```

```
<210> SEQ ID NO 8
<211> LENGTH: 645
<212> TYPE: DNA
<213> ORGANISM: Brassica napus
<220> FEATURE:
<223> OTHER INFORMATION: Bn INDEHISCENT2 (IND2) putative cDNA

<400> SEQUENCE: 8
atgtataaaa gaaaggtcta tgcgtctcta gtccaaaaac tctatatatg tctggctcaa     60
aagcagatgc agccatagcc ccaatagtca tgatggagca tcatcatctc cttatgaatt    120
ggaacaaacc tattgatctc attacagaag aaaactcttt taaccacaat cctcatttca    180
tagtagatcc accttccgaa accctaagca cttccagcc ccgccgaca atcttctccg    240 atcacggagg agagaggaa gcagaagaag aagaagaaga gaaggagag aagagatgg    300 atccgatgaa gaagatgcaa tacgcgattg ctgccatgca gcccgtagac ctcgatccag    360
ccaccgttcc taagccgaac cgccgtaacg taagggtaag cgacgaccct cagacggtgg    420
tggctcgtcg gcgtagagaa aggataagcg agaagatccg gatattgaag aggatggtgc    480
caggcggtgc aaagatggac actgcctcca tgctcgacga agccatcgc tacaccaagt    540 tcttgaaacg gcaggtgagg ctagcttctt cagcctcaca ctcagcttgg agctcctatg    600
tctgacccct tcttgctttg ttattaccac aactcggata cctaa                    645
```

```
<210> SEQ ID NO 9
<211> LENGTH: 210
<212> TYPE: PRT
<213> ORGANISM: Brassica napus
<220> FEATURE:
<223> OTHER INFORMATION: Bn INDEHISCENT1 (IND1) protein

<400> SEQUENCE: 9

Met Tyr Lys Arg Lys Val Tyr Ala Ser Leu Val Gln Lys Leu Tyr Met
 1               5                  10                  15

Ser Gly Ser Lys Ala Asp Ala Ala Ile Ala Pro Ile Val Met Met
            20                  25                  30

Glu Pro His His Leu Leu Met Asn Trp Asn Lys Pro Ile Asp Leu Ile
        35                  40                  45

Thr Gln Glu Asn Ser Phe Asn His Asn Pro His Phe Met Val Asp Pro
    50                  55                  60

Pro Ser Glu Thr Leu Ser His Phe Gln Pro Pro Thr Val Phe Ser
 65                 70                  75                  80

Asp Pro Gly Gly Gly Glu Ala Glu Asp Glu Gly Glu Glu
                85                  90                  95

Ile Asp Glu Met Lys Glu Met Gln Tyr Ala Ile Ala Ala Met Gln Pro
            100                 105                 110

Val Asp Ile Asp Pro Ala Thr Val Pro Lys Pro Asn Arg Arg Asn Val
        115                 120                 125

Arg Val Ser Glu Asp Pro Gln Thr Val Val Ala Arg Arg Arg Glu
    130                 135                 140

Arg Ile Ser Glu Lys Ile Arg Ile Leu Lys Arg Met Val Pro Gly Gly
145                 150                 155                 160

Ala Lys Met Asp Thr Ala Ser Met Leu Asp Glu Ala Ile Arg Tyr Thr
                165                 170                 175

Lys Phe Leu Lys Arg Gln Val Arg Leu Leu Gln Pro His Thr Gln Leu
            180                 185                 190

Gly Ala Pro Met Ser Asp Pro Ser Arg Leu Cys Tyr Tyr His Asn Ser
        195                 200                 205

Asp Thr
    210

<210> SEQ ID NO 10
<211> LENGTH: 171
<212> TYPE: PRT
<213> ORGANISM: Brassica napus
<220> FEATURE:
<223> OTHER INFORMATION: Bn INDEHISCENT2 (IND2) protein

<400> SEQUENCE: 10

Met Met Glu His His His Leu Leu Met Asn Trp Asn Lys Pro Ile Asp
 1               5                  10                  15

Leu Ile Thr Glu Glu Asn Ser Phe Asn His Asn Pro His Phe Ile Val
            20                  25                  30

Asp Pro Pro Ser Glu Thr Leu Ser His Phe Gln Pro Pro Thr Ile
        35                  40                  45

Phe Ser Asp His Gly Gly Glu Glu Ala Glu Glu Glu Glu Glu
    50                  55                  60

Glu Gly Glu Glu Glu Met Asp Pro Met Lys Lys Met Gln Tyr Ala Ile
 65                 70                  75                  80

Ala Ala Met Gln Pro Val Asp Leu Asp Pro Ala Thr Val Pro Lys Pro
                85                  90                  95
```

```
Asn Arg Arg Asn Val Arg Val Ser Asp Asp Pro Gln Thr Val Val Ala
            100                 105                 110
Arg Arg Arg Arg Glu Arg Ile Ser Glu Lys Ile Arg Ile Leu Lys Arg
            115                 120                 125
Met Val Pro Gly Gly Ala Lys Met Asp Thr Ala Ser Met Leu Asp Glu
    130                 135                 140
Ala Ile Arg Tyr Thr Lys Phe Leu Lys Arg Gln Val Arg Leu Ala Ser
145                 150                 155                 160
Ser Ala Ser His Ser Ala Trp Ser Ser Tyr Val
                165                 170

<210> SEQ ID NO 11
<211> LENGTH: 4225
<212> TYPE: DNA
<213> ORGANISM: Brassica napus
<220> FEATURE:
<223> OTHER INFORMATION: Bn INDEHISCENT1 (IND1) SK377

<400> SEQUENCE: 11
ttgatcgaaa cctcttcgca cagccgcatg aacttgccac cgacgacctc gtttcgccgg      60
agctcagaga ctgaagagcc tccaacgaaa ccatagctat tctacgccgc tctgtcttca     120
cgccggagag ttccatcgat ctaacgagat ctcctccgac tatgtatcac cacaaaccct     180
agacaggcga gccgagaacc actgatatcc tcctcttgta cgtcctcgcc gttgtcggag     240
agtttcatca tcatccgaga tctcatccgc gatgggccac gaccccatac ctgaccacaa     300
gaaccacacc gcacttatct cacctcgatc taatcaccac aacccaaagg acatcgggtt     360
ccaagacggc agcgcggagc tttgcaagcc tccactctcc gtgaccaaaa gccggcgaag     420
acggagctga atgagcctcc ccttcccgga agctaaagcg cgacggtgg atctgagaaa      480 gcctccacct cccgcataaa gaccggcgac gatggatcta gggtagcctc catctcccgg     540
aaaaaacacc acctgaacat gcaagccgct ccatctccac cgggagcctc caattgatcg     600
cgtcgttact ccaaaggccg agccaccgtt gatggatggt tgcggtccca gagctccgac     660
aaggcgatcg atgacgggac tgcgaagaag gagcggagtg tgacaactac aaaggaaggg     720
aaagagctct ggcgacagca cggacgctca cgcgccagcc gtacgccgaa cccaaaagta     780
gatctggttt ctctcttttc tctctctcgc aaaagaaaac acgcaaccta ttgttctcca     840
ttttgaattt gaagtgttac attattaata aaaaggaaga agtacaaag cttttcattt      900 agtggttgtt gcatatatag tatacttatt tgatgggctt atgataagta tgaacatttc     960
acgtaacggg tttattttgt cgtcaacaca ttaccggcaa tgtgaaaaga aggggcgagg    1020
tatctccatt tcaattcttc tctttataga ttaatcgaat tatttacata tgaaatgagc    1080
gtttatatag aattttcgtg tggaaaacga catgtacacg gcatcgaaag accaattagt    1140
aatatacttt agtggtgatt acatgtttac ttatccaatt gagaatttaa agcatcgaca    1200
ataccttaat gtcgattaag ccgtccccac ttcatgtaat gagttatggg gggagagaga    1260
ggtcccgaaa ttcgtcaaat aaaacaactt agaactaaaa accgacacca gtatcataa     1320 aggaaacgtt gaagaagtca tttatcgtat ccagctcaca attcctaaga ttaaatcatg    1380
accgttggaa gagcttataa gattaaattg aagaaattgt gggttttaga agaaagacaa    1440
gaaagagaag aacatgatct tacattgcct attttggtgt ataggagttg tcaaaaagag    1500
gagagagagg agacaattag gtcaaataaa tgagcactaa aaatgggagac atgtgttgag    1560 taactattac aagagcgact tatgcttcta tatggcaatg atatcatcac caaagtgcaa    1620
```

```
tgcccctttt tgccctagtt tcgtaaagtc tctttccttc ttcatcctta ggaaaaaccc    1680
taaattaaat cctgtgttct tgatcttgct ttttgagtaa ccatgatttt gaccacacac    1740
tagttcttct atattttgtg gtctatagga ttttgcttta tatgtgtttc ttgtattgca    1800
ccgtacgtgc gtatataaat ttaaatggtt acaacaaggt ttattataaa caggcacaaa    1860
ttagtccatg aggttattta gcttgcacaa gaggtatata atgtgtgtg tgtgtgttaa     1920
gtatttaaat atataaattt gctacaaaac ttaattaact ttatctgatt atattttctt    1980
tagtgttctt catttgccaa cgttgaggta gctattatta ttattattat tattattatt    2040
attattatta ttattattat tattattatt attattatta ttattattat tattattatt    2100
ttgaacatta tgtactatgt acgtagttat tttggctagt tatgattcaa attcttaatt    2160
tggataacac ttaacagtat ttaaaaaaaa aatactattt aaaatattct tagtactaaa    2220
ataattaaga tttaacttga aattgaagta ttcgtgttaa acagaaacta caataaacaa    2280
atgattgcat gttaattttt ttttcgatta tcctatatat cagaataaac acatgattgc    2340
atgcaaattt tgtttttgat tatgtcatct tttgtttatt ttagttttga tgctaattaa    2400
tatttttttt attaacaact tccatacatt ctacctgatt ctaggtcaga taatgacaca    2460
gcgcaacaaa attatacaaa actttcggaa agtagattac cgcggaagta acattttggg    2520
gtagacatac gaagtagttt gaatcttcaa aaatcatgcc atacataacc acggatcata    2580
gtcgacacct caacgtgaag caaatttgac aatctacata cataaccaac aaaaagtaga    2640
ataccgtgaa aacctaaacc caaaatatga tgaaaactca agctggtcca gagcataaaa    2700
aaattaaagc catcgctttg gtatcacata tttaaacgtc agtttttttt tggggaagta    2760
atataaaaat ataattaaca agaaaattta tgaaataatt agcatgtaaa acactagtct    2820
tttggttgtg acaaaacgtt ttcacaaatg ttctataaat aaattcaagc acattttatc    2880
tgcaaaatat atactttcac tcataaaata agagcgttta aaacattcat atacgcacta    2940
cattgacatg acaaaagaaa tccgcaaata caaacatatt tagttcggat atatctagga    3000
aataagacta tattatatat ataaagaaat tagaaaaaaa gaaaattggt atgtataaaa    3060
gaaggtcta  tgcgtctcta gtccaaaaac tctatatgtc tggttcaaaa gcagatgcag    3120
cagccatagc cccaatagtc atgatggagc ctcatcatct ccttatgaac tggaacaaac    3180
ctattgatct cattacacaa gaaaactctt ttaaccacaa tcctcatttc atggtagatc    3240
caccttccga aacccctaagc cacttccagc ccccgccgac agtcttctcc gatcccggag    3300
gaggagagga agcagaagac gaagaaggag aggaagagat agatgagatg aaggagatgc    3360
aatacgcgat tgctgccatg cagcccgtag acatcgatcc agccaccgtt cctaagccga    3420
accgccgtaa cgtaagggta agcgaggacc cccagacggt ggtggctcgt cggcgtagag    3480
aaaggataag cgagaagatc cggatattga agaggatggt gccaggcggt gcaaagatgg    3540
acactgcctc catgcttgac gaagccatcc gctacaccaa gttcttgaaa cggcaggtga    3600
ggcttcttca gcctcacact cagcttgggg ctcctatgtc tgacccttct cgcctttgtt    3660
attaccacaa ctcggatacc taattataat tctatcacgc gtttcatgtt gatatatata    3720
gataaatggt tgaataagga tttcgatcga agattgtatg gctattgatt acattatata    3780
ttgtacaata aatgatgtgt gtatttctat taatgtatat atgatatata tctgtttgca    3840
gtatgcattt atattctatt ctttataggg aggcaacatg ccggattagg gctttgatcg    3900
tatgcaagtt ttccgaccaa aaatatgaaa tacttgtttg gatataacat atgaatcgga    3960
taagtgttac tagttatata actggaaaaa aattgtttgg tataagaatt cccgggagaa    4020
```

-continued

```
ccaagccttt ctctaatccc taagatcata gctactggaa ataatgaaaa aaaacaaaaa    4080
aaaacaatga agaatcagtt gggcattagt ccaaaaaaaa aaagaatcag ttggatgctt    4140
ataaatttgt tataaattta tgtcgtatgt gtgttaccga aactgaaatt tattccttgg    4200
aggtaatgaa attaattata tccga                                          4225
```

<210> SEQ ID NO 12
<211> LENGTH: 4426
<212> TYPE: DNA
<213> ORGANISM: Brassica napus
<220> FEATURE:
<223> OTHER INFORMATION: Bn INDEHISCENT2 (IND2) SK378
<220> FEATURE:
<221> NAME/KEY: modified_base
<222> LOCATION: (1)..(4426)
<223> OTHER INFORMATION: n = g, a, c or t

<400> SEQUENCE: 12

```
gacaatcagt cagcgttana cattgcgtct aacccggtct atcatgaacg caccaagcat      60
gttgagatcg actgtcacat tgttcgggag cggttgcaga gcggcttcat gaaggctcta     120
cacgtccggt ctgagcttca gttagctgnn catattcact aaggttgttc aaccaggctt     180
gttcaagagt ttagtaagca agattggaat tcatagtcta tgcattccat cttgagggga     240
gggtattaga ttatggttaa gtgatggttt aataactggt ttagcttcct tttactaaac     300
cggttatata atacatcct cttgtacatt gtaaacttta acttgagcaa tatacttttt      360 cctttttcatc gtaacatact ttccccattg atcttgagct caagttctaa taaacatatt    420
acgtaacggg tttattttgt cgtcaacaca ttatcggcaa tgtgaaaaga aggggtgagg     480
tatctccatt tcaattcttc tctttatata ttaatcgaat tatttacgta tgaaatgaac     540
gtttatatag aaatttcgtg tggaaaacga catgtacacg gcatctcaag accaattagt     600
aatatacttt agtggtgatt acatgtttac ttatccaatt gagaatttaa agcatcgaca     660
ataccttaat gtcgattaag ccgtccccac ttcatgtaat gagttatggg gggagagaga     720
gatcccgaaa ttcgtcaaat aaaacaactt agaactaaaa ccgacaccaa gtatcataaa     780
ggaaatgttg aagaagtcat ttatcgtatc cagctcacaa ttcctaagat taaatcatga     840
ccgttggaag agcttataag attaaactga agaaattgtg ggttttagaa gaagacaag      900 aaagagaaga acatgatctt acattgccta ttttggtgta taggagttgt caaaaagagg     960
agagagagga gacaattagg tcaaataaat gagcactaaa aatggagaca tgtgttgagt    1020
aactattaca agagcgactt atgcttctat atggcaatga tatcatcacc aaagtgcaat    1080
gccccttttt gccctagttt cgtaaagtct ctctccttct tcgtccttag gaaaaaccct    1140
aaattaaatc ctgtgttctt gatctttctt tttgagtaac catgattttg accacacact    1200
agttcttcta tattttgtgg tctataggat tttgctttat atgtgttttct tgtattgctc    1260 cgtacgtgcg tatataaatt taaatggtta caacaaggtt tattataaat aggcacaaat    1320
tagtccatga agttatttag cttgcacaag tataatttgt taagtattta aatatataaa    1380
tttgttacaa aacttaatta aatttatctg attatatttt ctttagtgtt cttcctttgc    1440
caacgttgag gtagctatta ttattattat tttgaacatt atgtacgtag ttatcttggc    1500
tagttatgat tcgaattctt aatttggatc acacttaaca gtatttaaaa tattcttaga    1560
actaaaataa ttaagagtta cctttaaatt gaagtattcg tgctaaacag aaactagaat    1620
aaacaaatga ttgcatgtta attttttttt tcgatttcc tatcagaata aacacatgat     1680
```

```
tgcatgcaaa ttttgttttt gattacgtta tcttttgttt attttagttt tgatgctaat    1740 taatatttttt tattaacaac tcacatacat tctacctgat tctaggtcag ataatgacac    1800
agcgcaacaa aattaataca aaaccttcgg aaagtagaat accgcagaag taactttttt    1860
gggtacatac gaaatacagt gaaatctcta taaattaata atgttgggac tataccaaaa    1920 ctataattttt ttattaattt atagagatta atttatcgca tatactaatt gaatcaaaaa    1980
cttaatttga gactaaaaat tatattattt tatagagatt tttagtgtat attaatttat    2040
agaatattat tttataaaaa attttagtgt gtattaattt atagagtatt aatttaaaga    2100
ggttatactg taatgtgaat cttcgaaaaa catgccatac ataaccacgg atcatagtcg    2160
accctcaacg tgaagcaaat ttgacaatnt acatacataa ccaacaaaaa gtagaatacc    2220
ttgaaaatnt aaaacccaaa atatgatgta aaactcaagc ttggtccaga gcataaaaaa    2280
attaaagcca tcgctttggt atcacatatt taaacgtcag tttttttttt tttttttggg    2340 ggggggggg gggtaatat aaaaatataa ttaacaaaaa aaaattatga aacaattagc    2400
atgtaaaaca ctaatctttt ggttgtgaca aaacgttttc acaaatgttc tataaataaa    2460
ttcaagtgca ttttatctgc aaaatatata ctttcactca taaaataaga gcgtttaaaa    2520
cattcataca cgcactacat tgacatgaca aaagaaatcc gcaaatacac atgatgtatg    2580
tcgaaaaaaa caaaaaatac acatgatgta tatatagaga ggatagtatc taggaaataa    2640
gactatatta tatatataaa gaaaatagag aaaagataaa aatataaatt ggtatgtata    2700
aaagaaaggt ctatgcgtct ctagtccaaa aactctatat atgtctggct caaaagcaga    2760
tgcagccata gccccaatag tcatgatgga gcatcatcat ctccttatga attggaacaa    2820
acctattgat ctcattacag aagaaaactc ttttaaccac aatcctcatt tcatagtaga    2880
tccaccttcc gaaaccctaa gccacttcca gcccccgccg acaatcttct ccgatcacgg    2940
aggaggagag gaagcagaag aagaagaaga agaagaagga gaggaagaga tggatccgat    3000
gaagaagatg caatacgcga ttgctgccat gcagcccgta gacctcgatc cagccaccgt    3060
tcctaagccg aaccgccgta acgtaagggt aagcgacgac cctcagacgg tggtggctcg    3120
tcggcgtaga gaaaggataa gcgagaagat ccggatattg aagaggatgg tgccaggcgg    3180
tgcaaagatg gacactgcct ccatgctcga cgaagccatc cgctacacca agttcttgaa    3240
acggcaggtg aggctagctt cttcagcctc acactcagct tggagctcct atgtctgacc    3300
cttcttgcct ttgttattac cacaactcgg ataccctaatt ataattctat cacgcgtttc    3360
atgttgatat atatagataa atggtcgaat aaggatttcg atcgaagatt gtatgtacaa    3420
taaatgatgt gtgtatttca attaatgtat gatatatata tatatatgta tgcagtatgc    3480
atttatattc tattctctat aaggaggcaa cattgccgga ttagggcttt gatcttatgc    3540
aagttttccg accaaaaata tgaaatactt gtttggatat aacatatgaa tcggataagt    3600
gttactagtt atataactgg aaaacaaatg tctggaataa gaattcccgg gagaaccaag    3660
cctttctcta atccctaaga ttatagctac tgaaacaatg aaacaatgaa gaatcagttg    3720
ggcattagta aaaaaaaaag aatcagttgg gttgcttata aattttgtt ataaaattta    3780 tgtcgtatgt gtgttagccg tagctgtaaa tttatttcct ttgtatgtta attgtaaaag    3840
taaatttatt attcccgatg ttttttaatga tgtaaattta aatcaagaaa acatattaag    3900
ttctgttaat aaatgtatta tttttgttta ctaatttcca ataatttttt caagaagtac    3960
aattttttgt ttgaaatttc taatttatca ttattgaata atagaacata cctaaaaacc    4020
ataaaacatg tattccttga aacatttttt ttaatataaa aattatcttt taggagcagg    4080
```

```
taaagtactt ttttttataa aattgttagt gtatttatgt tcgttataga tgtagatatt   4140
ttgcataata attaataata tatgagatgt gtaatgtata tatgtgagag aattgccata   4200
tttattaagc ggttttgta aaattgactc aaaatttaaa gtcaaccaca aaactaacat    4260 atgtttttt ggacatttca tttgccctat tcactccaca agttcagatt atttacgaaa    4320
atgtcattat ttttttcttt tctgaaatgg tattttctc tctcaacctc atcatcttca    4380
gtatttcaag attgtcattg cctcaataac caccacctga acacca                  4426
```

<210> SEQ ID NO 13
<211> LENGTH: 200
<212> TYPE: PRT
<213> ORGANISM: Arabidopsis sp.
<220> FEATURE:
<223> OTHER INFORMATION: INDEHISCENT1 (IND1) protein

<400> SEQUENCE: 13

```
Met Lys Met Glu Asn Gly Met Tyr Lys Lys Lys Gly Val Cys Asp Ser
 1               5                  10                  15

Cys Val Ser Ser Lys Ser Arg Ser Asn His Ser Pro Lys Arg Ser Met
            20                  25                  30

Met Glu Pro Gln Pro His His Leu Leu Met Asp Trp Asn Lys Ala Asn
        35                  40                  45

Asp Leu Leu Thr Gln Glu His Ala Ala Phe Leu Asn Asp Pro His His
    50                  55                  60

Leu Met Leu Asp Pro Pro Pro Glu Thr Leu Ile His Leu Asp Glu Asp
65                  70                  75                  80

Glu Glu Tyr Asp Glu Asp Met Asp Ala Met Lys Glu Met Gln Tyr Met
                85                  90                  95

Ile Ala Val Met Gln Pro Val Asp Ile Asp Pro Ala Thr Val Pro Lys
            100                 105                 110

Pro Asn Arg Arg Asn Val Arg Ile Ser Asp Asp Pro Gln Thr Val Val
        115                 120                 125

Ala Arg Arg Arg Glu Arg Ile Ser Glu Lys Ile Arg Ile Leu Lys
    130                 135                 140

Arg Ile Val Pro Gly Gly Ala Lys Met Asp Thr Ala Ser Met Leu Asp
145                 150                 155                 160

Glu Ala Ile Arg Tyr Thr Lys Phe Leu Lys Arg Gln Val Arg Ile Leu
                165                 170                 175

Gln Pro His Ser Gln Ile Gly Ala Pro Met Ala Asn Pro Ser Tyr Leu
            180                 185                 190

Cys Tyr Tyr His Asn Ser Gln Pro
        195                 200
```

<210> SEQ ID NO 14
<211> LENGTH: 603
<212> TYPE: DNA
<213> ORGANISM: Arabidopsis sp.
<220> FEATURE:
<223> OTHER INFORMATION: INDEHISCENT1 (IND1) coding/rescue

<400> SEQUENCE: 14

```
atgaaaatgg aaaatggtat gtataaaaag aaaggagtgt gcgactcttg tgtctcgtcc    60
aaaagcagat ccaaccacag ccccaaaaga agcatgatgg agcctcagcc tcaccatctc   120
ctcatggatt ggaacaaagc taatgatctt ctcacacaag aacacgcagc ttttctcaat   180
gatcctcacc atctcatgtt agatccacct cccgaaaccc taattcactt ggacgaagac   240
```

```
gaagagtacg atgaagacat ggatgcgatg aaggagatgc agtacatgat cgccgtcatg    300
cagcccgtag acatcgaccc tgccacggtc cctaagccga accgccgtaa cgtaaggata    360
agcgacgatc ctcagacggt ggttgctcgt cggcgtcggg aaaggatcag cgagaagatc    420
cgaattctca agaggatcgt gcctggtggt gcgaagatgg acacagcttc catgctcgac    480
gaagccatac gttacaccaa gttcttgaaa cggcaggtga ggattcttca gcctcactct    540
cagattggag ctcctatggc taaccectct tacctttgtt attaccacaa ctcccaaccc    600
tga                                                                  603
```

<210> SEQ ID NO 15
<211> LENGTH: 665
<212> TYPE: DNA
<213> ORGANISM: Artificial Sequence
<220> FEATURE:
<223> OTHER INFORMATION: Description of Artificial Sequence:IND
      consensus sequence
<220> FEATURE:
<221> NAME/KEY: modified_base
<222> LOCATION: (39)
<223> OTHER INFORMATION: n = t or absent
<220> FEATURE:
<221> NAME/KEY: modified_base
<222> LOCATION: (40)
<223> OTHER INFORMATION: n = g or absent
<220> FEATURE:
<221> NAME/KEY: modified_base
<222> LOCATION: (41)
<223> OTHER INFORMATION: n = t or absent
<220> FEATURE:
<221> NAME/KEY: modified_base
<222> LOCATION: (42)
<223> OTHER INFORMATION: n = g or absent
<220> FEATURE:
<221> NAME/KEY: modified_base
<222> LOCATION: (77)
<223> OTHER INFORMATION: n = a or absent
<220> FEATURE:
<221> NAME/KEY: modified_base
<222> LOCATION: (78)
<223> OTHER INFORMATION: n = g or absent
<220> FEATURE:
<221> NAME/KEY: modified_base
<222> LOCATION: (79)
<223> OTHER INFORMATION: n = c or absent
<220> FEATURE:
<221> NAME/KEY: modified_base
<222> LOCATION: (95)
<223> OTHER INFORMATION: n = a or absent
<220> FEATURE:
<221> NAME/KEY: modified_base
<222> LOCATION: (96)
<223> OTHER INFORMATION: n = g or absent
<220> FEATURE:
<221> NAME/KEY: modified_base
<222> LOCATION: (111)
<223> OTHER INFORMATION: n = a or absent
<220> FEATURE:
<221> NAME/KEY: modified_base
<222> LOCATION: (112)
<223> OTHER INFORMATION: n = g or absent
<220> FEATURE:
<221> NAME/KEY: modified_base
<222> LOCATION: (113)..(114)
<223> OTHER INFORMATION: n = c or absent
<220> FEATURE:
<221> NAME/KEY: modified_base
<222> LOCATION: (115)
<223> OTHER INFORMATION: n = t or absent
<220> FEATURE:
<221> NAME/KEY: modified_base
<222> LOCATION: (116)
<223> OTHER INFORMATION: n = c or absent

```
<220> FEATURE:
<221> NAME/KEY: modified_base
<222> LOCATION: (170)
<223> OTHER INFORMATION: n = g or absent
<220> FEATURE:
<221> NAME/KEY: modified_base
<222> LOCATION: (171)
<223> OTHER INFORMATION: n = c or absent
<220> FEATURE:
<221> NAME/KEY: modified_base
<222> LOCATION: (172)
<223> OTHER INFORMATION: n = a or absent
<220> FEATURE:
<221> NAME/KEY: modified_base
<222> LOCATION: (193)..(194)
<223> OTHER INFORMATION: n = c or absent
<220> FEATURE:
<221> NAME/KEY: modified_base
<222> LOCATION: (195)
<223> OTHER INFORMATION: n = a or absent
<220> FEATURE:
<221> NAME/KEY: modified_base
<222> LOCATION: (251)
<223> OTHER INFORMATION: n = a, g or absent
<220> FEATURE:
<221> NAME/KEY: modified_base
<222> LOCATION: (264)
<223> OTHER INFORMATION: n = a, c or absent
<220> FEATURE:
<221> NAME/KEY: modified_base
<222> LOCATION: (280)
<223> OTHER INFORMATION: n = a or absent
<220> FEATURE:
<221> NAME/KEY: modified_base
<222> LOCATION: (281)
<223> OTHER INFORMATION: n = g or absent
<220> FEATURE:
<221> NAME/KEY: modified_base
<222> LOCATION: (282)
<223> OTHER INFORMATION: n = c or absent
<220> FEATURE:
<221> NAME/KEY: modified_base
<222> LOCATION: (283)
<223> OTHER INFORMATION: n = a or absent
<220> FEATURE:
<221> NAME/KEY: modified_base
<222> LOCATION: (284)
<223> OTHER INFORMATION: n = g or absent
<220> FEATURE:
<221> NAME/KEY: modified_base
<222> LOCATION: (285)..(286)
<223> OTHER INFORMATION: n = a or absent
<220> FEATURE:
<221> NAME/KEY: modified_base
<222> LOCATION: (287)
<223> OTHER INFORMATION: n = g or absent
<220> FEATURE:
<221> NAME/KEY: modified_base
<222> LOCATION: (288)
<223> OTHER INFORMATION: n = a or absent
<220> FEATURE:
<221> NAME/KEY: modified_base
<222> LOCATION: (583)
<223> OTHER INFORMATION: n = a or absent
<220> FEATURE:
<221> NAME/KEY: modified_base
<222> LOCATION: (584)
<223> OTHER INFORMATION: n = g or absent
<220> FEATURE:
<221> NAME/KEY: modified_base
<222> LOCATION: (585)
<223> OTHER INFORMATION: n = c or absent
<220> FEATURE:
<221> NAME/KEY: modified_base
<222> LOCATION: (586)
<223> OTHER INFORMATION: n = t or absent

<400> SEQUENCE: 15
```

```
atgtataaaa gaaaggtcta tgcgtctcta gtccaaaann nncdcthtat atgtctggtt      60
caaaagcaga tgcagcnnnc atagccccaa tagtnncatg atggagcctc nnnnnnatca    120
tctccttatg aattggaaca aacctattga tctcattaca caagaaaacn nntcttttaa    180
ccacaatcct cannntttca tggtagatcc accttccgaa accctaagcc acttccagcc    240
cccgccgaca ntcttctccg atcncggagg aggagaggan nnnnnnnnag aagaagacga    300
agaaggagag gaaagagatgg atgcgatgaa ggagatgcaa tacgcgattg ctgccatgca    360
gcccgtagac atcgatccag ccaccgttcc taagccgaac cgccgtaacg taagggtaag    420
cgacgaccct cagacggtgg tggctcgtcg gcgtagagaa aggataagcg agaagatccg    480
gatattgaag aggatggtgc caggcggtgc aaagatggac actgcctcca tgctcgacga    540
agccatccgc tacaccaagt tcttgaaacg gcaggtgagg ctnnnntctt cagcctcaca    600
ctcagcttgg agctcctatg tctgaccctt cttgcctttg ttattaccac aactcggata    660
cctaa                                                                 665

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence:example
      sequence

<400> SEQUENCE: 16
atgatggagc atcat                                                       15

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence:encoded by
      example sequence

<400> SEQUENCE: 17

Met Met Glu His His
 1               5

<210> SEQ ID NO 18
<211> LENGTH: 51
<212> TYPE: PRT
<213> ORGANISM: Artificial Sequence
<220> FEATURE:
<223> OTHER INFORMATION: Description of Artificial Sequence:Arabidopsis
      IND1 helix-loop-helix (HLH) DNA binding domain

<400> SEQUENCE: 18

Ile Ser Asp Asp Pro Gln Thr Val Val Ala Arg Arg Arg Arg Glu Arg
 1               5                  10                  15

Ile Ser Glu Lys Ile Arg Ile Leu Lys Arg Ile Val Pro Gly Gly Ala
                20                  25                  30

Lys Met Asp Thr Ala Ser Met Leu Asp Glu Ala Ile Arg Tyr Thr Lys
            35                  40                  45

Phe Leu Lys
        50

<210> SEQ ID NO 19
<211> LENGTH: 26
<212> TYPE: DNA
<213> ORGANISM: Artificial Sequence
```

```
<220> FEATURE:
<223> OTHER INFORMATION: Description of Artificial Sequence:PCR primer
      for amplification of genomic region of Arabidopsis
      IND1 or IND1 cDNA

<400> SEQUENCE: 19
gatgaaaatg gaaaatggta tgtata                                         26

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence:PCR primer
      for amplification of genomic region of Arabidopsis
      IND1 or IND1 cDNA

<400> SEQUENCE: 20
gttcatcagg gttgggagtt gtg                                            23

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence:5' RACE
      oligo

<400> SEQUENCE: 21
gagttgtggt aataacaaag gtaag                                          25

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence:PCR
      additional nested oligo

<400> SEQUENCE: 22
ggcttcgtcg agcatggaag c                                              21

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence:PCR
      additional nested oligo

<400> SEQUENCE: 23
gagcaaccac cgtctgagga tcg                                            23

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence:3' RACE PCR
      nested primer

<400> SEQUENCE: 24
ccctgccacg gtccctaagc                                                20

<210> SEQ ID NO 25
<211> LENGTH: 33
<212> TYPE: DNA
```

```
<213> ORGANISM: Artificial Sequence
<220> FEATURE:
<223> OTHER INFORMATION: Description of Artificial Sequence:oligo for
      PCR amplification of full-length IND cDNA

<400> SEQUENCE: 25
cgtcgacgat gaaaatggaa aatggtatgt ata                          33

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence:oligo for
      PCR amplification of full-length IND cDNA

<400> SEQUENCE: 26
cggatccgtt catcagggtt gggagttgtg                              30

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence:oligo for
      PCR amplification of IND product

<400> SEQUENCE: 27
gagcaaccac cgtctgagga tcg                                     23

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence:oligo for
      PCR amplification of IND product

<400> SEQUENCE: 28
cgtcgacgat gaaaatggaa aatggtatgt ata                          33
```

CONTROL OF FRUIT DEHISCENCE IN PLANTS BY *INDEHISCENT1* GENES

CROSS-REFERENCES TO RELATED APPLICATIONS

This application is a continuation-in-part of U.S. application Ser. No. 09/548,971, filed on Apr. 13, 2000, which is a continuation-in-part of U.S. application Ser. No. 09/339,998, filed on Jun. 25, 1999, now U.S. Pat. No. 6,410,826, which claims benefit of priority to U.S. Provisional Application No. 60/090,649, filed Jun. 25, 1998, each of which is incorporated by reference in its entirety.

STATEMENT AS TO RIGHTS TO INVENTIONS MADE UNDER FEDERALLY SPONSORED RESEARCH OR DEVELOPMENT

This invention was made with Government support under National Science Foundation Grant number IBN-9985530. The Government has certain rights in the invention.

BACKGROUND OF THE INVENTION

Rapeseed is one of the most important oilseed crops after soybeans and cottonseed, representing 10% of the world oilseed production in 1990. Rapeseed contains 40% oil, which is pressed from the seed, leaving a high-protein seed meal of value for animal feed and nitrogen fertilizer. Rapeseed oil, also known as canola oil, is a valuable product, representing the fourth most commonly traded vegetable oil in the world.

Unfortunately, the yield of seed from rapeseed and related plants is limited by pod dehiscence, which is a process that occurs late in fruit development whereby the pod is opened and the enclosed seeds released. Degradation and separation of cell walls along a discrete layer of cells dividing the two halves of the pod, termed the "dehiscence zone," result in separation of the two halves of the pod and release of the contained seeds. The dehiscence zone is a region of only one to three cells in width that extends along the entire length of the valve/replum boundary (Meakin and Roberts, *J. Exp. Botany* 41:995–1002 (1990)). As the cells in the dehiscence zone separate from one another, the valves detach from the replum, allowing seeds to be dispersed. Seed "shattering," whereby seeds are prematurely shed through dehiscence before the crop can be harvested, is a significant problem faced by commercial seed producers and represents a loss of income to the industry. Adverse weather conditions can exacerbate the process of dehiscence, resulting in greater than 50% loss of seed yield.

The fruit, a complex structure unique to flowering plants, mediates the maturation and dispersal of seeds. In most flowering plants, the fruit consists of the pericarp, which is derived from the ovary wall, and the seeds, which develop from fertilized ovules. *Arabidopsis*, which is typical of the more than 3000 species of the *Brassicaceae*, produces fruit in which the two carpel valves (ovary walls) are joined to the replum, a visible suture that divides the two carpels.

The plant hormone ethylene is produced by developing seeds and appears to be an important regulator of the dehiscence process. One line of evidence supporting a role for ethylene in regulation of dehiscence comes from studies of fruit ripening, which, like fruit dehiscence, is a process involving the breakdown of cell wall material. In fruit ripening, ethylene acts in part by activating cell wall degrading enzymes such as polygalacturonase (Theologis et al., *Develop. Genetics* 14:282–295 (1993)). Moreover, in genetically modified tomato plants in which the ethylene response is blocked, such as transgenic tomato plants expressing antisense polygalacturonase, there is a significant delay in fruit ripening (Lanahan et al., *The Plant Cell* 6:521–530 (1994); Smith et al., *Nature* 334:724–726 (1988)).

In dehiscence, ultrastructural changes that culminate in degradation of the middle lamella of dehiscence zone cell walls weaken rapeseed pods and eventually lead to pod shatter. As in fruit ripening, hydrolytic enzymes including polygalacturonases play a role in this programmed breakdown. For example, in oilseed rape, a specific endo-polygalacturonase, RDPG1, is upregulated and expressed exclusively in the dehiscence zone late in pod development (Petersen et al., *Plant Mol. Biol.* 31:517–527 (1996), which is incorporated herein by reference). Ethylene may regulate the activity of hydrolytic enzymes involved in the process of dehiscence as it does in fruit ripening (Meakin and Roberts, *J. Exp. Botany* 41:1003–1011 (1990), which is incorporated herein by reference). Yet, until now, the proteins that control the process of dehiscence, such as those regulating the relevant hydrolytic enzymes, have eluded identification.

Attempts to solve the problem of pod shatter and early fruit dehiscence over the past 20 years have focused on the breeding of shatter-resistant varieties. However, these plant hybrids are frequently sterile and lose favorable characteristics that must be regained by backcrossing, which is both time-consuming and laborious. Other strategies to alleviate pod shattering include the use of chemicals such as pod sealants or mechanical techniques such as swathing to reduce wind-stimulated shattering. To date, however, a simple method for producing genetically modified plants that do not open and release their seeds prematurely has not been described.

Thus, a need exists for identifying genes that regulate the dehiscence process and for developing genetically modified plant varieties in which the natural seed dispersal process is delayed. The present invention satisfies this need and provides related advantages as well.

BRIEF SUMMARY OF THE INVENTION

The present invention provides isolated nucleic acids comprising an IND1 polynucleotide encoding an polypeptide at least 60% identical to SEQ ID NO:2.

The present invention also provides expression cassettes comprising a promoter operably linked to a polynucleotide, or a complement thereof, wherein the polynucleotide is at least 60% identical to at least 200 contiguous nucleotides of a sequence encoding SEQ ID NO:2. In some embodiments, the sequence is SEQ ID NO:1. In some embodiments, the polynucleotide is at least 60% identical to a nucleotide sequence encoding SEQ ID NO:2. In some embodiments, the promoter is constitutive. In some embodiments, the promoter is tissue specific. In some embodiments, the promoter is a dehiscence zone specific promoter.

The present invention also provides plants comprising a recombinant expression cassette, the expression cassette comprising a promoter operably linked to a polynucleotide, or a complement thereof, wherein the polynucleotide is at least 60% identical to at least 200 contiguous nucleotides of a sequence encoding SEQ ID NO:2. In some embodiments, the sequence is SEQ ID NO:1. In some embodiments, the polynucleotide is at least 60% identical to a nucleotide sequence encoding SEQ ID NO:2. In some embodiments, the polynucleotide is operably linked to the promoter in the antisense orientation. In some embodiments, the polynucleotide is operably linked to the promoter in the sense orientation. In some embodiments, the plant further comprises a second polynucleotide at least 60% identical to at least 200 contiguous nucleotides of a sequence encoding SEQ ID NO:2, wherein the second polynucleotide is operably linked to a second promoter in the antisense orientation. In some embodiments, lignification is reduced in valve margin cells of the plant. In some embodiments, lignification is enhanced in the plant. In some embodiments, the promoter is a dehiscence zone-selective regulatory element. In some embodiments, the promoter is constitutive. In some embodiments, the plant is a *Brassica* species. In some embodiments, the plant is characterized by delayed seed dehiscence compared to a plant not comprising the expression cassette.

The present invention also provides methods of delaying fruit dehiscence in a plant. In some embodiments, the methods comprise suppressing expression of an IND1 nucleic acid in the plant by introducing into the plant a recombinant expression cassette comprising a promoter operably linked to a polynucleotide, or a complement thereof, wherein the polynucleotide is at least 60% identical to at least 200 contiguous nucleotides of a sequence encoding SEQ ID NO:2; and selecting a plant with delayed fruit dehiscence compared to a plant in which the expression cassette has not been introduced. In some embodiments, the polynucleotide is at least 60% identical to a nucleotide sequence encoding SEQ ID NO:2. In some embodiments, the sequence is SEQ ID NO:1. In some embodiments, the polynucleotide encoding the IND1 polypeptide is operably linked to the promoter in the antisense orientation. In some embodiments, the polynucleotide encoding the IND1 polypeptide is operably linked to the promoter in the sense orientation. In some embodiments, the polynucleotide further comprises a second polynucleotide at least 60% identical to at least 200 contiguous nucleotides of a sequence encoding SEQ ID NO:2, wherein the second polynucleotide is operably linked to a second promoter in the antisense orientation. In some embodiments, lignification is reduced in valve margin cells. In some embodiments, the promoter is a dehiscence zone-selective regulatory element. In some embodiments, the recombinant expression cassette is introduced into the plant using *Agrobacterium*. In some embodiments, the plant is a *Brassica* species.

Definitions

The terms "nucleic acid" and "polynucleotide" are used synonymously and refer to a single or double-stranded polymer of deoxyribonucleotide or ribonucleotide bases read from the 5' to the 3' end. Nucleic acids or polynucleotides may also include modified nucleotides that permit correct read through by a polymerase and do not alter expression of a polypeptide encoded by that nucleic acid. "Polynucleotide sequence" or "nucleic acid sequence" may include both the sense and antisense strands of a nucleic acid as either individual single strands or in the duplex. It includes, but is not limited to, self-replicating plasmids, chromosomal sequences, and infectious polymers of DNA or RNA.

The phrase "nucleic acid sequence encoding" refers to a nucleic acid that codes for an amino acid sequence of at least 5 contiguous amino acids within one reading frame. The amino acid need not necessarily be expressed when introduced into a cell or other expression system, but may merely be determinable based on the genetic code. For example, the sequence ATGATGGAGCATCAT (SEQ ID NO:16) encodes MMEHH. Thus, a polynucleotide may encode a polypeptide sequence that comprises a stop codon or contains a changed frame so long as at least 5 contiguous amino acids within one reading frame. The nucleic acid sequences may include both the DNA strand sequence that is transcribed into RNA and the RNA sequence that is translated into protein. The nucleic acid sequences include both the full length nucleic acid sequences as well as fragments from the full length sequences. It should be further understood that the sequence includes the degenerate codons of the native sequence or sequences which may be introduced to provide codon preference in a specific host cell.

The term "promoter" or "regulatory element" refers to a region or sequence determinants located upstream or downstream from the start of transcription and which are involved in recognition and binding of RNA polymerase and other proteins to initiate transcription. A "plant promoter" is a promoter capable of initiating transcription in plant cells. Such promoters need not be of plant origin, for example, promoters derived from plant viruses, such as the CaMV35S promoter, can be used in the present invention.

As used herein, the term "dehiscence zone-selective regulatory element" refers to a nucleotide sequence that, when operatively linked to a nucleic acid molecule, confers selective expression upon the operatively linked nucleic acid molecule in a limited number of plant tissues, including the valve margin or dehiscence zone. The valve margin is the future site of the dehiscence zone and encompasses the margins of the outer replum as well as valve cells adjacent to the outer replum. The dehiscence zone, which develops in the region of the valve margin, refers to the group of cells that separate during the process of dehiscence, allowing valves to come apart from the replum and the enclosed seeds to be released. Thus, a dehiscence zone-selective regulatory element, as defined herein, confers selective expression in the mature dehiscence zone, or confers selective expression in the valve margin, which marks the future site of the dehiscence zone.

A dehiscence zone-selective regulatory element can confer specific expression exclusively in cells of the valve margin or dehiscence zone or can confer selective expression in a limited number of plant cell types including cells of the valve margin or dehiscence zone. A SHATTERPROOF1 or SHATTERPROOF2 (SHP1 and SHP2, previously designated as AGL1 and AGL5, repectively) regulatory element, for example, which confers selective expression in ovules and placenta as well as in the dehiscence zone, is a dehiscence zone-selective regulatory element as defined herein. Similarly, an IND1 regulatory element also confers selective expression in the dehiscence zone. A dehiscence zone-selective regulatory element generally is distinguished from other regulatory elements by conferring selective expression in the valve margin or dehiscence zone without conferring expression throughout the adjacent carpel valves.

It is understood that limited modifications can be made without destroying the biological function of a regulatory element and that such limited modifications can result in dehiscence zone-selective regulatory elements that have substantially equivalent or enhanced function as compared to a wild type IND1 regulatory element. These modifications can be deliberate, as through site-directed mutagenesis, or can be accidental such as through mutation in hosts harboring the regulatory element. All such modified nucleotide sequences are included in the definition of a dehiscence zone-selective regulatory element as long as the ability to confer selective expression in the valve margin or dehiscence zone is substantially retained.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

The term "seed plant" means an angiosperm or gymnosperm. An angiosperm is a seed-bearing plant whose seeds are borne in a mature ovary (fruit). An angiosperm commonly is recognized as a flowering plant. Angiosperms are divided into two broad classes based on the number of cotyledons, which are seed leaves that generally store or absorb food. Thus, a monocotyledonous angiosperm is an angiosperm having a single cotyledon, whereas a dicotyledonous angiosperm is an angiosperm having two cotyledons. A variety of angiosperms are known including, for example, oilseed plants, leguminous plants, fruit-bearing plants, ornamental flowers, cereal plants and hardwood trees, which general classes are not necessarily exclusive. The skilled artisan will recognize that the methods of the invention can be practiced using these or other angiosperms, as desired. A gymnosperm is a seed-bearing plant with seeds not enclosed in an ovary.

The phrase "host cell" refers to a cell from any organism. Exemplary host cells are derived from plants, bacteria, yeast, fungi, insects or other animals. Methods for introducing polynucleotide sequences into various types of host cells are well known in the art.

The term "delayed," as used herein in reference to the timing of seed dispersal in a fruit produced by a non-naturally occurring plant of the invention, means a statistically significantly later time of seed dispersal as compared to the time seeds normally are dispersed from a corresponding plant at the same developmental stage expressing naturally-occurring levels of IND1. Thus, the term "delayed" is used broadly to encompass both seed dispersal that is significantly postponed as compared to the seed dispersal in a corresponding plant, and to seed dispersal that is completely precluded, such that fruits never release their seeds unless there is human or other intervention.

It is recognized that there can be natural variation of the time of seed dispersal within a plant species or variety. However, a "delay" in the time of seed dispersal in a non-naturally occurring plant of the invention readily can be identified by sampling a population of the non-naturally occurring plants and determining that the normal distribution of seed dispersal times is significantly later, on average, than the normal distribution of seed dispersal times in a population of the corresponding plant species or variety that does not contain an exogenous IND1 polynucleotide. Thus, production of non-naturally occurring plants of the invention provides a means to skew the normal distribution of the time of seed dispersal from pollination, such that seeds are dispersed, on average, at least about 1%, 2%, 5%, 10%, 30%, 50%, 100%, 200% or 500% later than in the corresponding plant species that does not contain an exogenous nucleic acid molecule encoding an IND1 gene product.

The term "suppressed" or "decreased" encompasses the absence of IND1 protein in a plant, as well as protein expression that is present but reduced as compared to the level of IND1 protein expression in a wild type plant. Furthermore, the term suppressed refers to IND1 protein expression that is reduced throughout the entire domain of IND1 expression, or to expression that is reduced in some part of the IND1 expression domain, provided that the resulting plant is characterized by delayed seed dispersal. The term "suppressed" also encompasses an amount of IND1 protein that is equivalent to wild type IND1 expression, but where the IND1 protein has a reduced level of activity. As discussed above, IND1 each contain a conserved an basic HLH domain; point mutations or gross deletions within the HLH domain that reduce the DNA-binding activity of IND1 can reduce or destroy the activity of IND1 and, therefore, "suppress" IND1 expression as defined herein. One skilled in the art will recognize that, preferably, IND1 expression is essentially absent in the valve margin of a plant or the IND1 protein is essentially non-functional.

"Increased" or "enhanced" IND1 activity or expression of a IND1 gene refers to an augmented change in IND1 activity. Examples of such increased activity or expression include the following. IND1 activity or expression of the IND1 gene is increased above the level of that in wild-type, non-transgenic control plants (i.e. the quantity of IND1 activity or expression of the IND1 gene is increased). IND1 activity or expression of the IND1 gene is in an organ, tissue or cell where it is not normally detected in wild-type, non-transgenic control plants (i.e. spatial distribution of IND1 activity or expression of the IND1 gene is increased). IND1 activity or expression is increased when IND1 activity or expression of the IND1 gene is present in an organ, tissue or cell for a longer period than in a wild-type, non-transgenic controls (i.e. duration of IND1 activity or expression of the IND1 gene is increased).

A polynucleotide sequence is "heterologous to" a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant, or a predecessor generation of the plant, by any means other than by a sexual cross. An exogenous nucleic acid molecule can have a naturally occurring or non-naturally occurring nucleotide sequence and can be a heterologous nucleic acid molecule derived from a different plant species than the plant into which the nucleic acid molecule is introduced or can be a nucleic acid molecule derived from the same plant species as the plant into which it is introduced. Examples of means by which this can be accomplished are described below, and include *Agrobacterium*-mediated transformation, biolistic methods, electroporation, in planta techniques, and the like.

An "IND1 polynucleotide" is a nucleic acid sequence substantially similar to SEQ ID NO:1, 7, 8, 11, or 12 or that encodes a bHLH polypeptide that is substantially similar to SEQ ID NO:2, 9 or 10. IND1 polypeptides will generally have an alanine at site 9 of the basic region of the protein (e.g., amino acid position 127 of SEQ ID NO:2, position 139 of SEQ ID NO:9 and position 112 of SEQ ID NO:10) and generally does not comprise a PAS domain (Nambu (1991) Cell 67:1157–1167; Wilk, R. (1996) Genes Dev. 10:93–102). IND polynucleotides may comprise (or consist of) a coding region of about 50 to about 10,000 or more nucleotides, sometimes from about 100 to about 3,000 nucleotides and sometimes from about 200 to about 600 nucleotides, which hybridizes to SEQ ID NO:1, 7 or 8 under stringent conditions (as defined below), or which encodes an IND1 polypeptide or fragment of at least 15 amino acids thereof. IND1 polynucleotides can also be identified by their ability to hybridize under low stringency conditions (e.g., Tm ~40° C.) to nucleic acid probes having the sequence of SEQ ID NO:1, 7, 8, 11, or 12. SEQ ID NO:1, 7, 8, 11, or 12 are examples of IND1 polynucleotides.

A "promoter from a IND1 gene" or "IND1 promoter" will typically be about 500 to about 3000 nucleotides in length, usually from about 750 to 2750. Exemplary promoter sequences are shown as SEQ ID NO:3 and SEQ ID NO:4. SEQ ID NO:3 represents the 5' untranslated region of the IND1 and SEQ ID NO:4 represents the 3' untranslated region of IND1. A IND1 promoter can also be identified by its ability to direct expression in the valve margin of fruit. In particular, the IND1 promoter directs expression at the valve margin of developing gynoecium just prior to fertilization (stage 13) through the maturation of the fruit (stage 17). The promoter does not provide significant expression in leaf tissue.

An "IND 1 polypeptide" is an amino acid sequence that is substantially similar to SEQ ID NOs:2, 9, or 10, or a fragment thereof. Active IND polypeptides generally have an alanine at site 9 of the basic region of the protein (e.g., amino acid position 129 of SEQ ID NO:2) and do not comprise a PAS domain (Nambu (1991) Cell 67:1157–1167; Wilk, R. (1996) Genes Dev. 10:93–102) Full-length IND1 polypeptides are characterized by the presence of an basic helix-loop-helix (HLH) domain which bind specific polynucleotide sequences. For instance amino acid residues ISDDPQTVVARRRRERISEKIR-ILKRIVPGGAKMDTASMLDEAIRYTKFLK (SEQ ID NO:18) represent the HLH domain of the polypeptide shown in SEQ ID NO:2. The HLH domain is known in the art and is shared by other transcription factors including uncharacterized sequences represented by GenBank accession number E1283552 and 2262147 and the gene product, PIF3 (Ni et al. Cell 95:657 (1998)). The HLH domain of IND1 is therefore a DNA binding domain.

As used herein, a homolog or ortholog of a particular IND1 gene (e.g., SEQ ID NO:1) is a second gene in the same plant type or in a different plant type, which has a polynucleotide sequence of at least 50 contiguous nucleotides which are substantially identical (determined as described below) to a sequence in the first gene. It is believed that, in general, homologs or orthologs share a common evolutionary past.

A "polynucleotide sequence from" a particular gene is a subsequence or full length polynucleotide sequence of an IND1 gene which, when present in a transgenic plant, has the desired effect. For example, one effect is inhibition of expression of the endogenous gene driving expression of an heterologous polynucleotide.

The term "reproductive tissues" as used herein includes fruit, ovules, seeds, pollen, pistols, flowers, or any embryonic tissue.

An "expression cassette" refers to a nucleic acid construct, which when introduced into a host cell, results in transcription and/or translation of a RNA or polypeptide, respectively. Antisense constructs or sense constructs that are not or cannot be translated are expressly included by this definition.

In the case of both expression of transgenes and inhibition of endogenous genes (e.g., by antisense, or sense suppression) one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the term "polynucleotide sequence from" a particular valve-margin gene, such as IND1. In addition, the term specifically includes sequences (e.g., full length sequences) substantially identical (determined as described below) with a IND1 gene sequence and that encode proteins that retain the function of a IND1 polypeptide.

In the case of polynucleotides used to inhibit expression of an endogenous gene, the introduced sequence need not be perfectly identical to a sequence of the target endogenous gene. The introduced polynucleotide sequence will typically be at least substantially identical (as: determined below) to the target endogenous sequence.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Optimal alignment of sequences for comparison may be conducted by the local homology algorithm of Smith and Waterman Add. APL. Math. 2:482 (1981), by the homology alignment algorithm of Needle man and Wunsch J. Mol. Biol. 48:443 (1970), by the search for similarity method of Pearson and Lipman Proc. Natl. Acad. Sci. (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 25% sequence identity. Alternatively, percent identity can be any integer from 25% to 100%. Exemplary embodiments include at least: 25%, 30%, 35%, 40%, 45%, 50%, 55%, 60%, 65%, 70%, 75%, 80%, 85% 90%, 95%, or 99%, compared to a reference sequence using the programs described herein; preferably BLAST using standard parameters, as described below. Accordingly, IND1 sequences of the invention include nucleic acid sequences that have substantial identity to SEQ ID NO:1, 7, 8, 11 or 12. IND1 sequences of the invention also include polypeptide sequences having substantial identify to SEQ ID NO:2, 9 or 10. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%. Preferred percent identity of polypeptides can be any integer from 40% to 100%, e.g., at least 40%, 45%, 50%, 55%, 60%, 65%, 70%, 75%, 80%, 85%, 90%, 95%, or 99%, an sometimes at least 61%, 62%, 63%, 64%, 65%, 66%, 67%, 68%, 69%, 70%, 71%, 72%, 73%, 74% and 75%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

In the present invention, mRNA encoded by IND1 genes of the invention can be identified in Northern blots under stringent conditions using cDNAs of the invention or fragments of at least about 100 nucleotides. For the purposes of this disclosure, stringent conditions for such RNA-DNA hybridizations are those which include at least one wash in 0.2×SSC at 63° C. for 20 minutes, or equivalent conditions. Genomic DNA or cDNA comprising genes of the invention can be identified using the same cDNAs (or fragments of at least about 100 nucleotides) under stringent conditions, which for purposes of this disclosure, include at least one wash (usually 2) in 0.2×SSC at a temperature of at least about 50° C., usually about 55° C., for 20 minutes, or equivalent conditions.

The term "isolated", when applied to a nucleic acid or protein, denotes that the nucleic acid or protein is essentially free of other cellular components with which it is associated in the natural state. It is preferably in a homogeneous state and may be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest.

BRIEF DESCRIPTION OF THE DRAWINGS

FIG. 2 depicts an alignments of the nucleotide sequence of *Arabidopsis* IND1 (nucleotides 2765–3361 of SEQ ID NO:1) with the *Brassica napus* amino acid sequences of Bn IND1 (SEQ ID NO:7) and Bn IND2 (SEQ ID NO:8).

DETAILED DESCRIPTION OF THE INVENTION

I. Introduction

Figure 1:
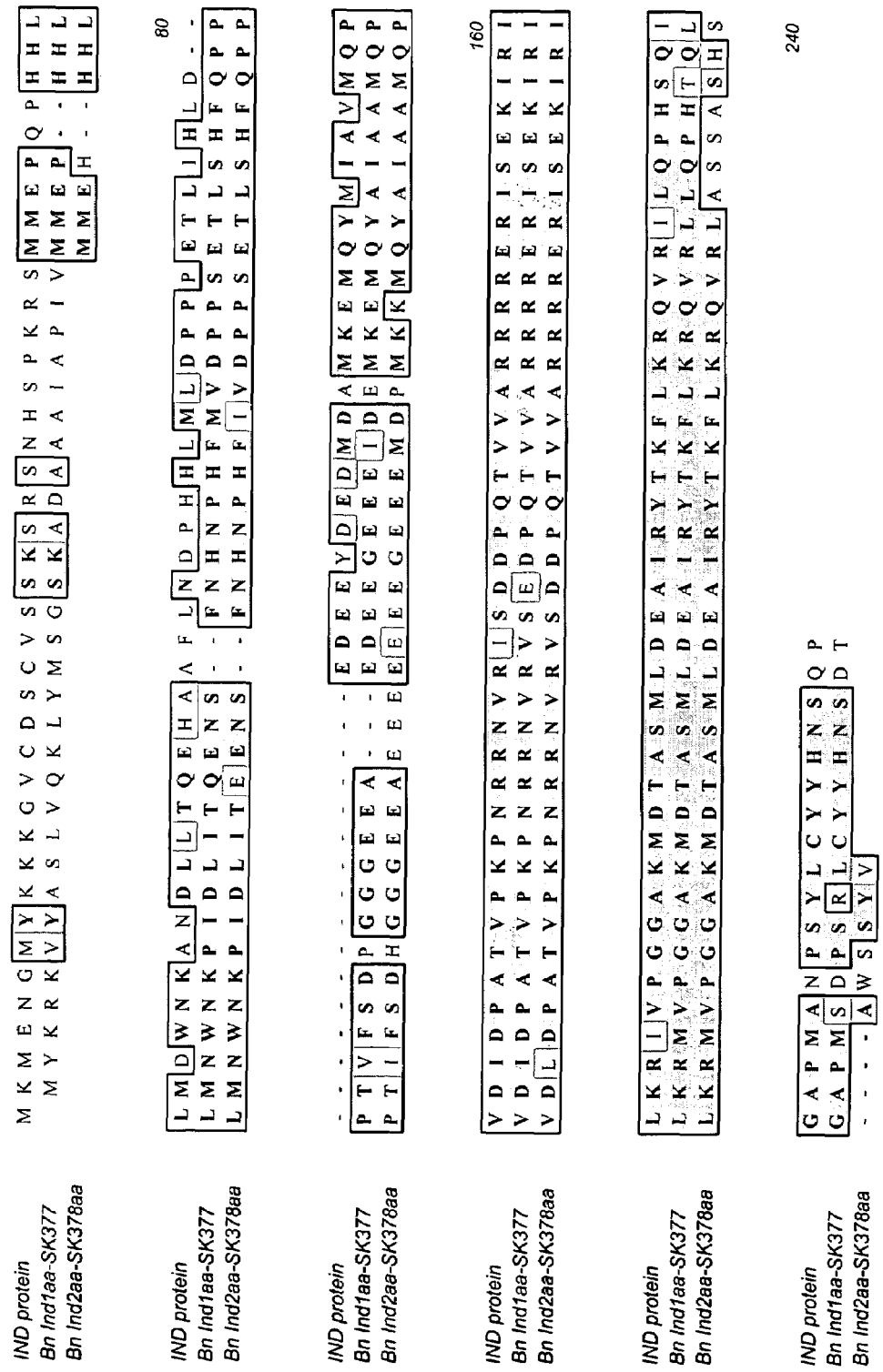
FIG. 1 depicts an alignments of the amino acid sequence of *Arabidopsis* IND1 (SEQ ID NO:2) with the *Brassica napus* amino acid sequences of Bn IND1 (SEQ ID NO:9) and Bn IND2 (SEQ ID NO:10).

The present invention provides methods of modulating fruit development in plants. In particular, the invention provides methods of delaying or preventing fruit dehiscence by suppressing expression of an bHLH gene such as IND1 in a plant. The invention also provides transgenic plants comprising various polynucleotides encoding an bHLH polypeptide such as IND1.

The present invention relates to the previous discovery that an agl1 agl5 double mutant plant has a delayed seed dispersal phenotype (Liljegren et al., Nature 404:766–770 (2000)). Loss-of-function mutations in the SHP1 and SHP2 genes were produced by disruptive T-DNA insertion and homologous recombination. In the resulting shp1 shp2 double mutant plants, the dehiscence zone failed to develop normally, and the mature fruits did not undergo dehiscence. Thus, SHP1 or SHP2 gene expression is required for development of the dehiscence zone. These results indicate that SHP1 and SHP2 regulate pod dehiscence and that manipulation of SHP1 and SHP2 expression can allow the process of pod shatter to be controlled.

The present invention provides evidence that IND1 is regulated by SHP1 and SHP2 and that expression of IND1 modulates fruit dehiscence. The present invention also provides for methods of delaying fruit dehiscence by suppressing expression of IND1. The invention also provides for methods of modulating lignification in plants by modulating IND1 expression.

The *Arabidopsis* SHP1 and SHP2 genes encode MADS box proteins with 85% identity at the amino acid level. The SHP1 and SHP2 RNA expression patterns are also strikingly similar. In particular, both RNAs are specifically expressed in flowers, where they accumulate in developing carpels. In particular, strong expression of these genes is observed in the outer replum along the valve/replum boundary (Ma et al., supra, 1991; Savidge et al., The Plant Cell 7:721–723 (1995); Flanagan et al., The Plant Journal 10:343–353 (1996), each of which is incorporated herein by reference). Thus, SHP1 and SHP2 are expressed in the valve margin, at least within the cells of the outer replum.

Generally, the nomenclature and the laboratory procedures in recombinant DNA technology described below are those well known and commonly employed in the art.

Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., Molecular Cloning—A Laboratory Manual, 2nd. ed., Cold Spring Harbor Laboratory, Cold Spring Harbor, N.Y., (1989) and Current Protocols in Molecular Biology, F. M. Ausubel et al., eds., Current Protocols, a joint venture between Greene Publishing Associates, Inc. and John Wiley & Sons, Inc., (supplemented through 2004).

II. Isolation of Nucleic Acids of the Invention

The isolation of polynucleotides of the invention may be accomplished by a number of techniques. For instance, oligonucleotide probes based on the sequences disclosed here can be used to identify the desired polynucloetide in a cDNA or genomic DNA library from a desired plant species. To construct genomic libraries, large segments of genomic DNA are generated by random fragmentation, e.g. using restriction endonucleases, and are ligated with vector DNA to form concatemers that can be packaged into the appropriate vector. Alternatively, cDNA libraries from plants or plant parts (e.g., flowers) may be constructed.

The cDNA or genomic library can then be screened using a probe based upon the sequence of a cloned IND1 gene such as the polynucleotides disclosed here. Probes may be used to hybridize with genomic DNA or cDNA sequences to isolate homologous genes in the same or different plant species.

Alternatively, the nucleic acids of interest can be amplified from nucleic acid samples using amplification techniques. For instance, polymerase chain reaction (PCR) technology to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying genes such as IND1 from plant tissues are generated from comparisons of the sequences provided herein. For a general overview of PCR see PCR Protocols: A Guide to Methods and Applications. (Innis, M, Gelfand, D., Sninsky, J. and White, T., eds.), Academic Press, San Diego (1990). Appropriate primers for amplification of the genomic region of Arabidopsis IND1 or the IND1 cDNA include the following primer pairs: 5'-gatgaaaatggaaaatggtatgtata-3' (SEQ ID NO:19) and 5'-gttcatcagggttgggagttgtg-3' (SEQ ID NO:20). The amplification conditions are typically as follows. Reaction components: 10 mM Tris-HCl, pH 8.3, 50 mM potassium chloride, 1.5 mM magnesium chloride, 0.001% gelatin, 200 µM dATP, 200 µM dCTP, 200 µM dGTP, 200 µM dTTP, 0.4 µM primers, and 100 units per ml Taq polymerase. Program: 96 C for 3 mm., 30 cycles of 96 C for 45 sec., 50 C for 60 sec., 72 for 60 sec, followed by 72 C for 5 mm.

Polynucleotides may also be synthesized by well-known techniques as described in the technical literature. See, e.g., Carruthers et al., Cold Spring Harbor Symp. *Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

The genus of IND1 nucleic acid sequences of the invention includes genes and gene products identified and characterized by analysis using nucleic acid sequences of the invention, including SEQ ID NO:1, 7, 8 11, and 12 and protein sequences of the invention, including SEQ ID NO:2, 9 and 10. IND1 sequences of the invention include nucleic acid sequences having substantial identity to SEQ ID NO:1, 7, 8 11, and/or 12. IND1 sequences of the invention also include polypeptide sequences having substantial identity to SEQ ID NO: 2, 9 and/or 10.

III. Use of Nucleic Acids of the Invention

A. Use of Nucleic Acids of the Invention to Inhibit or Suppress Gene Expression

The invention provides methods of modulating fruit dehiscence in a plant by introducing into a plant a recombinant expression cassette comprising a regulatory element operably linked to a IND1 polynucleotide. The invention also provides methods for delaying seed dispersal in a plant by suppressing expression of a nucleic acid molecule encoding an IND1 gene product. In a transgenic plant of the invention, a nucleic acid molecule, or antisense constructs thereof, encoding an IND1 gene product can be operatively linked to an exogenous regulatory element. The invention provides, for example, a transgenic plant characterized by delayed seed dispersal having an expressed nucleic acid molecule encoding an IND1 gene product, or antisense construct thereof, that is operatively linked to an exogenous constitutive regulatory element. In one embodiment, the invention provides a transgenic plant that is characterized by delayed seed dispersal and/or modulated lignification due to suppression of a nucleic acid molecule encoding an IND1 polypeptide. In some embodiments, suppression of IND1 expression results in reduced lignification in cells adjacent to the dehiscence zone (e.g., valve margin cells, see, e.g., U.S. application Ser. No. 09/339,998, filed on Jun. 25, 1999), whereas ectopic expression results in increased lignification.

The IND1 sequences of the invention can be used to prepare expression cassettes useful in a number of techniques, including inhibiting, suppressing or increasing, expression or for ectopic expression. A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The expression cassette is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al., *Proc. Nat. Acad. Sci. USA*, 85:8805–8809 (1988); Pnueli et al., *The Plant Cell* 6:175–186 (1994); and Hiatt et al., U.S. Pat. No. 4,801,340.

The antisense nucleic acid sequence transformed into plants will be substantially identical to at least a portion of the endogenous gene or genes to be repressed. The sequence, however, does not have to be perfectly identical to inhibit expression. Thus, an antisense or sense nucleic acid molecule encoding only a portion of IND1 can be useful for producing a plant in which IND1 expression is suppressed. The vectors of the present invention can be designed such that the inhibitory effect applies to other proteins within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of IND1 genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. *Nature,* 334:585–591 (1988).

Another method of suppression is sense suppression (also known as co-suppression). Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al., *The Plant Cell* 2:279–289 (1990); Flavell, *Proc. Natl. Acad. Sci., USA* 91:3490–3496 (1994); Kooter and Mol, *Current Opin. Biol.* 4:166–171 (1993); and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence in the expression cassette, needing less than absolute identity, also need not be full length, relative to either the primary transcription product or fully processed mRNA. This may be preferred to avoid concurrent production of some plants that are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

Endogenous gene expression may also be suppressed by means of RNA interference (RNAi), which uses a double-stranded RNA having a sequence identical or similar to the sequence of the target gene. RNAi is the phenomenon in which when a double-stranded RNA having a sequence identical or similar to that of the target gene is introduced into a cell, the expressions of both the inserted exogenous gene and target endogenous gene are suppressed. The double-stranded RNA may be formed from two separate complementry RNAs or may be a single RNA with internally complementary sequences that form a double-stranded RNA. Although details of the mechanism of RNAi are still unknown, it is considered that the introduced double-stranded RNA is initially cleaved into small fragments, which then serve as indexes of the target gene in some manner, thereby degrading the target gene. RNAi is known to be also effective in plants (see, e.g., Chuang, C. F. & Meyerowitz, E. M., *Proc. Natl. Acad. Sci. USA* 97: 4985 (2000); Waterhouse et al., *Proc. Natl. Acad. Sci. USA* 95:13959–13964 (1998); Tabara et al. *Science* 282:430–431 (1998)). For example, to achieve suppression of the expression of a DNA encoding a protein using RNAi, a double-stranded RNA having the sequence of a DNA encoding the protein, or a substantially similar sequence thereof (including those engineered not to translate the protein) or fragment thereof, is introduced into a plant of interest. The resulting plants may then be screened for a phenotype associated with the target protein and/or by monitoring steady-state RNA levels for transcripts encoding the protein. Although the genes used for RNAi need not be completely identical to the target gene, they may be at least 70%, 80%, 90%, 95% or more identical to the target gene sequence. See, e.g., U.S. Patent Publication No. 2004/0029283. The constructs encoding an RNA molecule with a stem-loop structure that is unrelated to the target gene and that is positioned distally to a sequence specific for the gene of interest may also be used to inhibit target gene expression. See, e.g., U.S. Patent Publication No. 2003/0221211.

The RNAi polynucleotides may encompass the full-length target RNA or may correspond to a fragment of the target RNA. In some cases, the fragment will have fewer than 100, 200, 300, 400, 500 600, 700, 800, 900 or 1,000 nucleotides corresponding to the target sequence. In some cases, fragments for use in RNAi will be at least substantially similar to regions of a target protein that do not occur in other proteins in the organism or may be selected to have as little similarity to other organism transcripts as possible, e.g., selected by comparison to sequences in analyzing publicly-available sequence databases. Thus, RNAi fragments may be selected for similarity or identity with the N terminal region of the IND1 and BIND1 sequences of the invention (i.e., those sequences lacking significant homology to sequences in the databases) or may be selected for identity or similarity to coding sequences for the bHLH domain or at least sequences distinguishing the IND1 bHLH domain from other bHLH domain proteins.

Expression vectors that continually express siRNA in transiently- and stably-transfected have been engineered to express small hairpin RNAs, which get processed in vivo into siRNAs molecules capable of carrying out gene-specific silencing (Brummelkamp et al., *Science* 296:550–553 (2002), and Paddison, et al., *Genes & Dev.* 16:948–958 (2002)). Post-transcriptional gene silencing by double-stranded RNA is discussed in further detail by Hammond et al. *Nature Rev Gen* 2: 110–119 (2001), Fire et al. *Nature* 391: 806–811 (1998) and Timmons and Fire *Nature* 395: 854 (1998).

One of skill in the art will recognize that using technology based on specific nucleotide sequences (e.g., antisense or sense suppression technology), families of homologous genes can be suppressed with a single sense or antisense transcript. For instance, if a sense or antisense transcript is designed to have a sequence that is conserved among a family of genes: then multiple members of a gene family can be suppressed. Conversely, if the goal is to only suppress one member of a homologous gene family, then the sense or antisense transcript should be targeted to sequences with the most vairance between family members.

Another means of inhibiting IND1 function in a plant is by creation of dominant negative mutations. In this approach, non-functional, mutant IND1 polypeptides, which retain the ability to interact with wild-type subunits are introduced into a plant. A dominant negative construct also can be used to suppress IND1 expression in a plant. A dominant negative construct useful in the invention generally contains a portion of the complete IND1 coding sequence sufficient, for example, for DNA-binding or for a protein-protein interaction such as a homodimeric or heterodimeric protein-protein interaction but lacking the transcriptional activity of the wild type protein. For example, a carboxy-terminal deletion mutant of AGAMOUS was used as a dominant negative construct to suppress expression of the MADS box gene AGAMOUS (Mizukami et al., *Plant Cell* 8:831–844 (1996)). One skilled in the art understands that, similarly, a dominant negative IND1 construct can be used to suppress IND1 expression in a plant.

B. Use of Nucleic Acids of the Invention to Enhance Gene Expression

Isolated sequences prepared as described herein can also be used to prepare expression cassettes that enhance or increase endogenous IND1 gene expression. Where overexpression of a gene is desired, the desired gene from a different species may be used to decrease potential sense suppression effects. Enhanced expression of IND1 polynucleotides is useful, for example, to produce plants with small fruit.

Any of a number of means well known in the art can be used to increase IND1 activity in plants. Any organ can be targeted, such as shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit. Alternatively, one or several IND1 genes can be expressed constitutively (e.g., using the CaMV 35S promoter).

One of skill will recognize that the polypeptides encoded by the genes of the invention, like other proteins, have different domains which perform different functions. Thus, the gene sequences need not be full length, so long as the desired functional domain of the protein is expressed. As explained above, IND1 polypeptides carry a bHLH domain, which is capable of binding DNA. Thus, without being bound to any particular theory or mechanism, IND1 is likely to act as a transcriptional modulator.

C. Modification of Endogenous IND1 Genes

Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, X-rays or gamma rays can be used.

Modified protein chains can also be readily designed utilizing various recombinant DNA techniques well known to those skilled in the art and described for instance, in Sambrook et al., supra. Hydroxylamine can also be used to introduce single base mutations into the coding region of the gene (Sikorski, et al., (1991). *Meth. Enzymol.* 194: 302–318). For example, the chains can vary from the naturally occurring sequence at the primary structure level by amino acid substitutions, additions, deletions, and the like. These modifications can be used in a number of combinations to produce the final modified protein chain.

Alternatively, homologous recombination can be used to induce targeted gene modifications by specifically targeting the IND1 gene in vivo (see, generally, Grewal and Klar, *Genetics* 146: 1221–1238 (1997) and Xu et al., *Genes Dev.* 10: 2411–2422 (1996)). Homologous recombination has been demonstrated in plants (Puchta et al., *Experientia* 50: 277–284 (1994), Swoboda et al., *EMBO J.* 13: 484–489 (1994); Offringa et al., *Proc. Natl. Acad. Sci. USA* 90: 7346–7350 (1993); and Kempin et al. *Nature* 389:802–803 (1997)).

In applying homologous recombination technology to the genes of the invention, mutations in selected portions of an IND1 gene sequences (including 5' upstream, 3' downstream, and intragenic regions) such as those disclosed here are made in vitro and then introduced into the desired plant using standard techniques. Since the efficiency of homologous recombination is known to be dependent on the vectors used, use of dicistronic gene targeting vectors as described by Mountford et al., *Proc. Natl. Acad. Sci. USA* 91: 4303–4307 (1994); and Vaulont et al., *Transgenic Res.* 4: 247–255 (1995) are conveniently used to increase the efficiency of selecting for altered IND1 gene expression in transgenic plants. The mutated gene will interact with the target wild-type gene in such a way that homologous recombination and targeted replacement of the wild-type gene will occur in transgenic plant cells, resulting in suppression of IND1 activity.

Alternatively, oligonucleotides composed of a contiguous stretch of RNA and DNA residues in a duplex conformation with double hairpin caps on the ends can be used. The RNA/DNA sequence is designed to align with the sequence of the target IND1 gene and to contain the desired nucleotide change. Introduction of the chimeric oligonucleotide on an extrachromosomal T-DNA plasmid results in efficient and specific IND1 gene conversion directed by chimeric molecules in a small number of transformed plant cells. This method is described in Cole-Strauss et al., *Science* 273: 1386–1389 (1996) and Yoon et al., *Proc. Natl. Acad. Sci. USA* 93: 2071–2076 (1996).

In other embodiments, the promoters derived from the IND1 genes of the invention can be used to drive expression of heterologous genes in an valve margin-specific manner. Suitable structural genes that could be used for this purpose include genes encoding cytotoxic proteins as discussed below.

Typically, desired promoters are identified by analyzing the 5' sequences of a genomic clone corresponding to the IND1 genes described here. Sequences characteristic of promoter sequences can be used to identify the promoter.

Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation. In plants, further upstream from the TATA box, at positions −80 to −100, there is typically a promoter element with a series of adenines surrounding the trinucleotide G (or T) N G. J. Messing et al., in GENETIC ENGINEERING IN PLANTS, pp. 221–227 (Kosage, Meredith and Hollaender, eds. (1983)).

A number of methods are known to those of skill in the art for identifying and characterizing promoter regions in plant genomic DNA (see, e.g., Jordano, et al., *Plant Cell*, 1: 855–866 (1989); Bustos, et al., *Plant Cell*, 1:839–854 (1989); Green, et al., *EMBO J.* 7, 4035–4044 (1988); Meier, et al., *Plant Cell*, 3, 309–316 (1991); and Zhang, et al., *Plant Physiology* 110: 1069–1079 (1996)).

IV. Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill.

Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers. As noted above, the promoters from the IND1 genes described here are particularly useful for directing gene expression so that a desired gene product is located in the valve margin of fruit. Other suitable promoters include those from genes such as SHP1 or SHP2 (Savidge, B., Rounsley, S. D., and Yanofsky, M. F. (1995) *Plant Cell* 7: 721–733). Examples of environmental conditions that may affect transcription by inducible promoters include anaerobic conditions, elevated temperature, or the presence of light.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

IND1 nucleic acid sequences of the invention are expressed recombinantly in plant cells to enhance and increase levels of endogenous IND1 polypeptides. Alternatively, antisense or other IND1 constructs (described above) are used to suppress IND1 levels of expression. A variety of different expression constructs, such as expression cassettes and vectors suitable for transformation of plant cells can be prepared. Techniques for transforming a wide variety of higher plant species are well known and described in the technical and scientific literature. See, e.g., Weising et al. *Ann. Rev. Genet.* 22:421–477 (1988). A DNA sequence coding for a IND1 polypeptide, e.g., a cDNA sequence encoding a full length protein, can be combined with cis-acting (promoter) and trans-acting (enhancer) transcriptional regulatory sequences to direct the timing, tissue type and levels of transcription in the intended tissues of the transformed plant. Translational control elements can also be used.

The invention provides an IND1 nucleic acid operably linked to a promoter which, in a preferred embodiment, is capable of driving the transcription of the IND1 coding sequence in plants. The promoter can be, e.g., derived from plant or viral sources. The promoter can be, e.g., constitutively active, inducible, or tissue specific. In construction of recombinant expression cassettes, vectors, transgenics, of the invention, a different promoters can be chosen and employed to differentially direct gene expression, e.g., in some or all tissues of a plant or animal. Typically, as discussed above, desired promoters are identified by analyzing the 5' sequences of a genomic clone corresponding to the IND1 genes described here.

A. Constitutive Promoters

A promoter fragment can be employed which will direct expression of IND1 nucleic acid in all transformed cells or tissues, e.g. as those of a regenerated plant. The term "constitutive regulatory element" means a regulatory element that confers a level of expression upon an operatively linked nucleic molecule that is relatively independent of the cell or tissue type in which the constitutive regulatory element is expressed. A constitutive regulatory element that is expressed in a plant generally is widely expressed in a large number of cell and tissue types. Promoters that drive expression continuously under physiological conditions are referred to as "constitutive" promoters and are active under most environmental conditions and states of development or cell differentiation.

A variety of constitutive regulatory elements useful for ectopic expression in a transgenic plant are well known in the art. The cauliflower mosaic virus 35S (CaMV 35S) promoter, for example, is a well-characterized constitutive regulatory element that produces a high level of expression in all plant tissues (Odell et al., *Nature* 313:810–812 (1985)). The CaMV 35S promoter can be particularly useful due to its activity in numerous diverse plant species (Benfey and Chua, *Science* 250:959–966 (1990); Futterer et al., *Physiol. Plant* 79:154 (1990); Odell et al., supra, 1985). A tandem 35S promoter, in which the intrinsic promoter element has been duplicated, confers higher expression levels in comparison to the unmodified 35S promoter (Kay et al., *Science* 236:1299 (1987)). Other useful constitutive regulatory elements include, for example, the cauliflower mosaic virus 19S promoter; the Figwort mosaic virus promoter; and the nopaline synthase (nos) gene promoter (Singer et al., *Plant Mol. Biol.* 14:433 (1990); An, *Plant Physiol.* 81:86 (1986)).

Additional constitutive regulatory elements including those for efficient expression in monocots also are known in the art, for example, the pEmu promoter and promoters based on the rice Actin-1 5' region (Last et al., *Theor. Appl. Genet.* 81:581 (1991); Mcelroy et al., *Mol. Gen. Genet.* 231:150 (1991); Mcelroy et al., *Plant Cell* 2:163 (1990)). Chimeric regulatory elements, which combine elements from different genes, also can be useful for ectopically expressing a nucleic acid molecule encoding an IND1 polynucleotide (Comai et al., *Plant Mol. Biol.* 15:373 (1990)).

Other examples of constitutive promoters include the 1'- or 2'-promoter derived from T-DNA of *Agrobacterium tumafaciens* (see, e.g., Mengiste (1997) supra; O'Grady (1995) *Plant Mol. Biol.* 29:99–108); actin promoters, such as the *Arabidopsis* actin gene promoter (see, e.g., Huang (1997) *Plant Mol. Biol.* 1997 33:125–139); alcohol dehydrogenase (Adh) gene promoters (see, e.g., Millar (1996) *Plant Mol. Biol.* 31:897–904); ACT11 from *Arabidopsis* (Huang et al. *Plant Mol. Biol.* 33:125–139 (1996)), Cat3 from *Arabidopsis* (GenBank No. U43147, Zhong et al., *Mol. Gen. Genet.* 251:196–203 (1996)), the gene encoding stearoyl-acyl carrier protein desaturase from *Brassica napus* (Genbank No. X74782, Solocombe et al. *Plant Physiol.* 104:1167–1176 (1994)), GPc1 from maize (GenBank No. X15596, Martinez et al. *J. Mol. Biol* 208:551–565 (1989)), Gpc2 from maize (GenBank No. U45855, Manjunath et al., *Plant Mol. Biol.* 33:97–112 (1997)), other transcription initiation regions from various plant genes known to those of skill. See also Holtorf *Plant Mol. Biol.* 29:637–646 (1995).

B. Inducible Promoters

Alternatively, a plant promoter may direct expression of the IND1 nucleic acid of the invention under the influence of changing environmental conditions or developmental conditions. Examples of environmental conditions that may effect transcription by inducible promoters include anaerobic conditions, elevated temperature, drought, or the presence of light. Such promoters are referred to herein as "inducible" promoters. For example, the invention incorporates the drought-inducible promoter of maize (Busk (1997) supra); the cold, drought, and high salt inducible promoter from potato (Kirch (1997) *Plant Mol. Biol.* 33:897–909).

Alternatively, plant promoters which are inducible upon exposure to plant hormones, such as auxins, are used to express the nucleic acids of the invention. For example, the invention can use the auxin-response elements E1 promoter fragment (AuxREs) in the soybean (*Glycine max* L.) (Liu (1997) *Plant Physiol.* 115:397–407); the auxin-responsive *Arabidopsis* GST6 promoter (also responsive to salicylic acid and hydrogen peroxide) (Chen (1996) *Plant J.* 10: 955–966); the auxin-inducible parC promoter from tobacco (Sakai (1996) 37:906–913); a plant biotin response element (Streit (1997) *Mol. Plant Microbe Interact.* 10:933–937); and, the promoter responsive to the stress hormone abscisic acid (Sheen (1996) *Science* 274:1900–1902).

Plant promoters which are inducible upon exposure to chemicals reagents which can be applied to the plant, such as herbicides or antibiotics, are also used to express the nucleic acids of the invention. For example, the maize In2-2 promoter, activated by benzenesulfonamide herbicide safeners, can be used (De Veylder (1997) *Plant Cell Physiol.* 38:568–577); application of different herbicide safeners induces distinct gene expression patterns, including expression in the root, hydathodes, and the shoot apical meristem. IND1 coding sequence can also be under the control of, e.g., a tetracycline-inducible promoter, e.g., as described with transgenic tobacco plants containing the *Avena sativa* L. (oat) arginine decarboxylase gene (Masgrau (1997) *Plant J.* 11:465–473); or, a salicylic acid-responsive element (Stange (1997) *Plant J.* 11:1315–1324; Uknes et al., *Plant Cell* 5:159–169 (1993); Bi et al., *Plant J.* 8:235–245 (1995)).

Particularly useful inducible regulatory elements include copper-inducible regulatory elements (Mett et al., *Proc. Natl. Acad. Sci. USA* 90:4567–4571 (1993); Furst et al., *Cell* 55:705–717 (1988)); tetracycline and chlor-tetracycline-inducible regulatory elements (Gatz et al., *Plant J.* 2:397–404 (1992); Röder et al., *Mol. Gen. Genet.* 243:32–38 (1994); Gatz, *Meth. Cell Biol.* 50:411–424 (1995)); ecdysone inducible regulatory elements (Christopherson et al., *Proc. Natl. Acad. Sci. USA* 89:6314–6318 (1992); Kreutzweiser et al., *Ecotoxicol. Environ. Safety* 28:14–24 (1994)); heat shock inducible regulatory elements (Takahashi et al., *Plant Physiol.* 99:383–390 (1992); Yabe et al., *Plant Cell Physiol.* 35:1207–1219 (1994); Ueda et al., *Mol. Gen. Genet.* 250: 533–539 (1996)); and lac operon elements, which are used in combination with a constitutively expressed lac repressor to confer, for example, IPTG-inducible expression (Wilde et al., *EMBO J.* 11:1251–1259 (1992)). An inducible regulatory element useful in the transgenic plants of the invention also can be, for example, a nitrate-inducible promoter derived from the spinach nitrite reductase gene (Back et al., *Plant Mol. Biol.* 17:9 (1991)) or a light-inducible promoter, such as that associated with the small subunit of RuBP carboxylase or the LHCP gene families (Feinbaum et al., *Mol. Gen. Genet.* 226:449 (1991); Lam and Chua, *Science* 248:471 (1990)).

C. Tissue-Specific Promoters

Alternatively, the plant promoter may direct expression of the polynucleotide of the invention in a specific tissue (tissue-specific promoters). Tissue specific promoters are transcriptional control elements that are only active in particular cells or tissues at specific times during plant development, such as in vegetative tissues or reproductive tissues. Promoters from the IND1 genes of the invention are particularly useful for tissue-specific direction of gene expression so that a desired gene product is generated only or preferentially in embryos or seeds, as described below.

Examples of tissue-specific promoters under developmental control include promoters that initiate transcription only (or primarily only) in certain tissues, such as vegetative tissues, e.g., roots or leaves, or reproductive tissues, such as fruit, ovules, seeds, pollen, pistils, flowers, or any embryonic tissue. Reproductive tissue-specific promoters may be, e.g., ovule-specific, embryo-specific, endosperm-specific, integument-specific, seed and seed coat-specific, pollen-specific, petal-specific, sepal-specific, or some combination thereof.

The invention provides a transgenic plant that is characterized by delayed seed dispersal due to expression of a nucleic acid molecule encoding an IND1 gene product, or an antisense construct thereof, operatively linked to a dehiscence zone-selective regulatory element. The dehiscence zone-selective regulatory element can be, for example, an SHP1 regulatory element or SHP2 regulatory element. The SHP1 regulatory element can be derived from the *Arabidopsis* SHP1 genomic sequence disclosed herein as SEQ ID NO:5 and can be, for example, a 5' regulatory sequence or intronic regulatory element. Similarly, the SHP2 regulatory element can be derived from the *Arabidopsis* SHP2 genomic sequence disclosed herein as SEQ ID NO:6 and can be, for example, a 5' regulatory sequence or intronic regulatory element.

A dehiscence zone-selective regulatory element can be derived from a gene that is an ortholog of Arabidopsis IND1 and is selectively expressed in the valve margin or dehiscence zone of a seed plant. A dehiscence zone-selective regulatory element can be derived, for example, from an IND1 ortholog of the Brassicaceae, such as a Brassica napus, Brassica oleracea, Brassica campestris, Brassica juncea, Brassica nigra or Brassica carinata IND1 ortholog. A dehiscence zone-selective regulatory element can be derived, for example, from an IND1 canola ortholog. A dehiscence zone-selective regulatory element also can be derived, for example, from a leguminous IND1 ortholog, such as a soybean, pea, chickpea, moth bean, broad bean, kidney bean, lima bean, lentil, cowpea, dry bean, peanut, alfalfa, lucerne, birdsfoot trefoil, clover, stylosanthes, lotononis bainessii, or sainfoin IND1 ortholog.

Dehiscence zone-selective regulatory elements also can be derived from a variety of other genes that are selectively expressed in the valve margin or dehiscence zone of a seed plant. For example, the rapeseed gene RDPG1 is selectively expressed in the dehiscence zone (Petersen et al., Plant Mol. Biol. 31:517–527 (1996)). Thus, the RDPG1 promoter or an active fragment thereof can be a dehiscence zone-selective regulatory element as defined herein. Additional genes such as the rapeseed gene SAC51 also are known to be selectively expressed in the dehiscence zone; the SAC51 promoter or an active fragment thereof also can be a dehiscence zone-selective regulatory element of the invention (Coupe et al., Plant Mol. Biol. 23:1223–1232 (1993)). The skilled artisan understands that a regulatory element of any such gene selectively expressed in cells of the valve margin or dehiscence zone can be a dehiscence zone-selective regulatory element as defined herein.

Additional dehiscence zone-selective regulatory elements can be identified and isolated using routine methodology. Differential screening strategies using, for example, RNA prepared from the dehiscence zone and RNA prepared from adjacent pod material can be used to isolate cDNAs selectively expressed in cells of the dehiscence zone (Coupe et al., supra, 1993); subsequently, the corresponding genes are isolated using the cDNA sequence as a probe.

Enhancer trap or gene trap strategies also can be used to identify and isolate a dehiscence zone-selective regulatory element of the invention (Sundaresan et al., supra, 1995; Koncz et al., Proc. Natl. Acad. Sci. USA 86:8467–8471 (1989); Kertbundit et al., Proc. Natl. Acad. Sci. USA 88:5212–5216 (1991); Topping et al., Development 112: 1009–1019 (1991)). Enhancer trap elements include a reporter gene such as GUS with a weak or minimal promoter, while gene trap elements lack a promoter sequence, relying on transcription from a flanking chromosomal gene for reporter gene expression. Transposable elements included in the constructs mediate fusions to endogenous loci; constructs selectively expressed in the valve margin or dehiscence zone are identified by their pattern of expression. With the inserted element as a tag, the flanking dehiscence zone-selective regulatory element is cloned using, for example, inverse polymerase chain reaction methodology (see, for example, Aarts et al., Nature 363:715–717 (1993); see also, Ochman et al., "Amplification of Flanking Sequences by Inverse PCR," in Innis et al., supra, 1990). The Ac/Ds transposition system of Sundaresan et al., Genes. Devel. 9:1797–1810 (1995), can be particularly useful in identifying and isolating a dehiscence zone-selective regulatory element of the invention.

Dehiscence zone-selective regulatory elements also can be isolated by inserting a library of random genomic DNA fragments in front of a promoterless reporter gene and screening transgenic plants transformed with the library for dehiscence zone-selective reporter gene expression. The promoterless vector pROA97, which contains the npt gene and the GUS gene each under the control of the minimal 35S promoter, can be useful for such screening. The genomic library can be, for example, Sau3A fragments of Arabidopsis thaliana genomic DNA or genomic DNA from, for example, another Brassicaceae of interest (Ott et al., Mol. Gen. Genet. 223:169–179 (1990); Claes et al., The Plant Journal 1:15–26 (1991)).

Dehiscence zone-selective expression of a regulatory element of the invention can be demonstrated or confirmed by routine techniques, for example, using a reporter gene and in situ expression analysis. The GUS and firefly luciferase reporters are particularly useful for in situ localization of plant gene expression (Jefferson et al., EMBO J. 6:3901 (1987); Ow et al., Science 334:856 (1986)), and promoterless vectors containing the GUS expression cassette are commercially available, for example, from Clontech (Palo Alto, Calif.). To identify a dehiscence zone-selective regulatory element of interest such as an IND1 regulatory element, one or more nucleotide portions of the IND1 gene can be generated using enzymatic or PCR-based methodology (Glick and Thompson, supra, 1993; Innis et al., supra, 1990); the resulting segments are fused to a reporter gene such as GUS and analyzed as described above.

Other tissue-specific promoters include seed promoters. Suitable seed-specific promoters are derived from the following genes: MAC1 from maize (Sheridan (1996) Genetics 142:1009–1020); Cat3 from maize (GenBank No. L05934, Abler (1993) Plant Mol. Biol. 22:10131–1038); vivparous-1 from Arabidopsis (Genbank No. U93215); atmycl from Arabidopsis (Urao (1996) Plant Mol. Biol. 32:571–57; Conceicao (1994) Plant 5:493–505); napA from Brassica napus (GenBank No. J02798, Josefsson (1987) JBL 26:12196–1301); and the napin gene family from Brassica napus (Sjodahl (1995) Planta 197:264–271).

A variety of promoters specifically active in vegetative tissues, such as leaves, stems, roots and tubers, can also be used to express the IND1 nucleic acids of the invention. For example, promoters controlling patatin, the major storage protein of the potato tuber, can be used, see, e.g., Kim (1994) Plant Mol. Biol. 26:603–615; Martin (1997) Plant J. 11:53–62. The ORF13 promoter from Agrobacterium rhizogenes which exhibits high activity in roots can also be used (Hansen (1997) Mol. Gen. Genet. 254:337–343. Other useful vegetative tissue-specific promoters include: the tarin promoter of the gene encoding a globulin from a major taro (Colocasia esculenta L. Schott) corm protein family, tarin (Bezerra (1995) Plant Mol. Biol. 28:137–144); the curculin promoter active during taro corm development (de Castro (1992) Plant Cell 4:1549–1559) and the promoter for the tobacco root-specific gene TobRB7, whose expression is localized to root meristem and immature central cylinder regions (Yamamoto (1991) Plant Cell 3:371–382).

Leaf-specific promoters, such as the ribulose biphosphate carboxylase (RBCS) promoters can be used. For example, the tomato RBCS1, RBCS2 and RBCS3A genes are expressed in leaves and light-grown seedlings, only RBCS1 and RBCS2 are expressed in developing tomato fruits (Meier (1997) FEBS Lett. 415:91–95). A ribulose bisphosphate carboxylase promoters expressed almost exclusively in mesophyll cells in leaf blades and leaf sheaths at high levels, described by Matsuoka (1994) *Plant J.* 6:311–319, can be used. Another leaf-specific promoter is the light harvesting chlorophyll a/b binding protein gene promoter, see, e.g., Shiina (1997) *Plant Physiol.* 115:477–483; Casal (1998) *Plant Physiol.* 116:1533–1538. The *Arabidopsis thaliana* myb-related gene promoter (Atmyb5) described by Li (1996) *FEBS Lett.* 379:117–121, is leaf-specific. The Atmyb5 promoter is expressed in developing leaf trichomes, stipules, and epidermal cells on the margins of young rosette and cauline leaves, and in immature seeds. Atmyb5 mRNA appears between fertilization and the 16 cell stage of embryo development and persists beyond the heart stage. A leaf promoter identified in maize by Busk (1997) *Plant J.* 11:1285–1295, can also be used.

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems, described by Di Laurenzio (1996) *Cell* 86:423–433; and, Long (1996) *Nature* 379:66–69; can be used. Another useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto (1995) *Plant Cell.* 7:517–527). Also useful are kn1-related genes from maize and other species which show meristem-specific expression, see, e.g., Granger (1996) *Plant Mol. Biol.* 31:373–378; Kerstetter (1994) *Plant Cell* 6:1877–1887; Hake (1995) *Philos. Trans. R. Soc. Lond. B. Biol. Sci.* 350:45–51. For example, the *Arabidopsis thaliana* KNAT1 promoter. In the shoot apex, KNAT1 transcript is localized primarily to the shoot apical meristem; the expression of KNAT1 in the shoot meristem decreases during the floral transition and is restricted to the cortex of the inflorescence stem (see, e.g., Lincoln (1994) *Plant Cell* 6:1859–1876).

One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

In another embodiment, a IND1 nucleic acid is expressed through a transposable element. This allows for constitutive, yet periodic and infrequent expression of the constitutively active polypeptide. The invention also provides for use of tissue-specific promoters derived from viruses which can include, e.g., the tobamovirus subgenomic promoter (Kumagai (1995) *Proc. Natl. Acad. Sci. USA* 92:1679–1683; the rice tungro bacilliform virus (RTBV), which replicates only in phloem cells in infected rice plants, with its promoter which drives strong phloem-specific reporter gene expression; the cassava vein mosaic virus (CVMV) promoter, with highest activity in vascular elements, in leaf mesophyll cells, and in root tips (Verdaguer (1996) *Plant Mol. Biol.* 31:1129–1139).

V. Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al. *EMBO J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

*Agrobacterium tumefaciens*-mediated transformation techniques, including disarming and use of binary vectors, are well described in the scientific literature. See, for example Horsch et al. *Science* 233:496–498 (1984), and Fraley et al. *Proc. Natl. Acad. Sci. USA* 80:4803 (1983).

Transformed plant cells which are derived by any of the above transformation techniques can be cultured to regenerate a whole plant which possesses the transformed genotype and thus the desired phenotype such as seedlessness. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124–176, MacMillilan Publishing Company, New York, 1983; and Binding, Regeneration of Plants, Plant Protoplasts, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The nucleic acids of the invention can be used to confer desired traits on essentially any plant. Thus, the invention has use over a broad range of plants, including species from the genera *Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna*, and, *Zea*. A useful plant of the invention can be a dehiscent seed plant, and a particularly useful plant of the invention can be a member of the Brassicaceae, such as rapeseed, or a member of the Fabaceae, such as a soybean, pea, lentil or bean plant.

In one embodiment, the invention provides a dehiscent seed plant that is characterized by delayed seed dispersal due to suppressed expression of a nucleic acid molecule encoding an IND1 gene product in the dehiscent seed plant. As used herein, the term "dehiscent seed plant" means a plant that produces a dry dehiscent fruit, which has fruit walls that open to permit escape of the seeds contained therein. Dehiscent fruits commonly contain several seeds and include the fruits known, for example, as legumes, capsules and siliques.

In one embodiment, the invention provides a plant that is characterized by delayed seed dispersal due to suppressed expression of a nucleic acid molecule encoding an IND1 gene product (e.g., substantially identical to SEQ ID NOs:2, 9, or 10), where the plant is a member of the Brassicaceae. The Brassicaceae, commonly known as the *Brassicas*, are a diverse group of crop plants with great economic value worldwide (see, for example, Williams and Hill, *Science* 232:1385–1389 (1986), which is incorporated herein by reference). The Brassicaceae produce seed oils for margarine, salad oil, cooking oil, plastic and industrial uses; condiment mustard; leafy, stored, processed and pickled vegetables; animal fodders and green manures for soil rejuvenation. A particularly useful non-naturally occurring *Brassica* plant of the invention is the oilseed plant canola.

There are six major *Brassica* species of economic importance, each containing a range of plant forms. *Brassica napus* includes plants such as the oilseed rapes and rutabaga. *Brassica oleracea* are the cole crops such as cabbage, cauliflower, kale, kohlrabi and Brussels sprouts. *Brassica campestris* (*Brassica rapa*) includes plants such as Chinese cabbage, turnip and pak choi. *Brassica juncea* includes a variety of mustards; *Brassica nigra* is the black mustard; and *Brassica carinata* is Ethiopian mustard. The skilled artisan understands that any member of the Brassicaceae can be modified as disclosed herein to produce a non-naturally occurring *Brassica* plant characterized by delayed seed dispersal.

In a second embodiment, the invention provides a plant that is characterized by delayed seed dispersal due to suppressed expression of a nucleic acid molecule encoding an IND1 gene product, where the plant is a member of the Fabaceae. The Fabaceae, which are commonly known as members of the pea family, are plants that produce a characteristic dry dehiscent fruit known as a legume. The legume is derived from a single carpel and dehisces along the suture of the carpel margins and along the median vein. The Fabaceae encompass both grain legumes and forage legumes. Grain legumes include, for example, soybean (glycine), pea, chickpea, moth bean, broad bean, kidney bean, lima bean, lentil, cowpea, dry bean and peanut. Forage legumes include alfalfa, lucerne, birdsfoot trefoil, clover, *stylosanthes* species, *lotononis bainessii* and sainfoin. The skilled artisan will recognize that any member of the Fabaceae can be modified as disclosed herein to produce a non-naturally occurring plant of the invention characterized by delayed seed dispersal.

A non-naturally occurring plant of the invention characterized by delayed seed dispersal also can be a member of the plant genus *Cuphea* (family Lythraceae). A *Cuphea* plant is particularly valuable since *Cuphea* oilseeds contain industrially and nutritionally important medium-chain fatty acids, especially lauric acid, which is currently supplied only by coconut and palm kernel oils.

A non-naturally occurring plant of the invention also can be, for example, one of the monocotyledonous grasses, which produce many of the valuable small-grain cereal crops of the world. Suppression of IND expression as described above, can be useful in generating a non-naturally occurring small grain cereal plant, such as a barley, wheat, oat, rye, orchard grass, guinea grass, sorghum or turf grass plant characterized by delayed seed dispersal.

VI. Additional Modifications that Modulate Seed Dispersal

It should be recognized that a plant of the invention, which contains an exogenous IND1 polynucleotide, also can contain one or more additional modifications, including naturally and non-naturally occurring modifications, that can modulate the delay in seed dispersal. For example, the plant hormone ethylene promotes fruit dehiscence, and modified expression or activity of positive or negative regulators of the ethylene response can be included in a plant of the invention (see, generally, Meakin and Roberts, *J. Exp. Botany* 41:1003–1011 (1990); Ecker, *Science* 268:667–675 (1995); Chao et al., *Cell* 89:1133–1144 (1997)).

Mutations in positive regulators of the ethylene response show a reduction or absence of responsiveness to treatment with exogenous ethylene. *Arabidopsis* mutations in positive regulators of the ethylene response include mutations in etr, which inactivate a histidine kinase ethylene receptor (Bleeker et al., *Science* 241:1086–1089 (1988); Schaller and Bleeker, *Science* 270:1809–1811 (1995)); ers (Hua et al., *Science* 269:1712–1714 (1995)); ein2 (Guzman and Ecker, *Plant Cell* 2:513 (1990)); ein3 (Rothenberg and Ecker, *Sem. Dev. Biol. Plant Dev. Genet.* 4:3–13 (1993); Kieber and Ecker, *Trends Genet.* 9:356–362 (1993)); ain1 (van der Straeten et al., *Plant Physiol.* 102:401–408 (1993)); eti (Harpham et al., *An. Bot.* 68:55 (1991)) and ein4, ein5, ein6, and ein7 (Roman et al., *Genetics* 139: 1393–1409 (1995)). Similar genetic functions are found in other plant species; for example, the never-ripe mutation corresponds to etr and confers ethylene insensitivity in tomato (Lanahan et al., *The Plant Cell* 6:521–530 (1994); Wilkinson et al., *Science* 270:1807–1809 (1995)). A plant of the invention can include a modification that results in altered expression or activity of any such positive regulator of the ethylene response. A mutation in a positive regulator, for example, can be included in a plant of the invention and can modify the delay in seed dispersal in such plants, for example, by further postponing the delay in seed dispersal.

Mutations in negative regulators of the ethylene response display ethylene responsiveness in the absence of exogenous ethylene. Such mutations include those relating to ethylene overproduction, for example, the eto 1, eto2, and eto3 mutants, and those relating to constitutive activation of the ethylene signalling pathway, for example, mutations in CTR1, a negative regulator with sequence similarity to the Raf family of protein kinases (Kieber et al., *Cell* 72:427–441 (1993), which is incorporated herein by reference). A plant of the invention can include a modification that results in altered expression or activity of any such negative regulator of the ethylene response. A mutation resulting in ethylene responsiveness in the absence of exogenous ethylene, for example, can be included in a non-naturally occurring plant of the invention and can modify, for example, diminish, the delay in seed dispersal.

Fruit morphological mutations also can be included in a plant of the invention. Such mutations include those in carpel identity genes such as AGAMOUS (Bowman et al., supra, 1989; Yanofsky et al., supra, 1990) and in genes required for normal fruit development such as ETTIN, CRABS CLAW, SPATULA, AGL8 and TOUSLED (Sessions et al., *Development* 121:1519–1532 (1995); Alvarez and Smyth, *Flowering Newsletter* 23:12–17 (1997); and Roe et al., *Cell* 75:939–950 (1993)). Thus, it is understood that a plant of the invention can include one or more additional genetic modifications, which can diminish or enhance the delay in seed dispersal.

EXAMPLES

The following examples are offered to illustrate, but no to limit the claimed invention.

Example 1

The GT140 valve margin marker (Sundaresan, V., et al. *Genes Dev.* 9, 1797–1810 (1995)) is expressed at the valve margin of the developing gynoecium just prior to fertilization (stage 13) and this pattern persists in the mature fruit (stage 17). As expression of this marker is largely absent from the valve margins of shp1 shp2 indehiscent fruits (Liljegren, S. J., et al. *Nature*, 404(6779):766–70 (2000)), it was expected that the gene corresponding to this marker might also be involved in valve margin development and be required for fruit dehiscence.

To isolate flanking genomic sequence from the GT140 marker insertion site, TAIL/PCR was performed as previously described (Tsugeki, R., et al. *Plant J.* 10, 479–489 (1996)). Subsequent sequencing of the isolated PCR products demonstrated that they correspond to a fully sequenced BAC from chromosome 4, available in the public database as part of the *Arabidopsis* Genome Initiative. The GT140 insertion is located between two genes, one encoding a predicted basic helix-loop-helix (bHLH) transcription factor and the other representing a novel gene.

Through several lines of subsequent investigation, it was confirmed that the bHLH transcription factor (herein referred to as IND1 as noted below) was the relevant gene (SEQ ID NO:1). Promoter/enhancer::GUS fusions of the IND1 gene were introduced into wild-type plants and found to express GUS in an identical pattern to that of the GT140 marker line. Interestingly, approximately 25% of the transgenic lines failed to express significant GUS activity and displayed an indehiscent phenotype. The most likely explanation of these results is that the IND1::GUS fusions, as well as of the endogenous IND1 gene, were cosuppressed. Subsequent RNA blotting confirmed a down regulation of the IND1 gene in these lines, and further RNA blotting showed, as expected, a decrease in IND1 gene expression in shp1 shp2 fruits.

In parallel to the studies of the GT140 valve margin marker described above, screens for *Arabidopsis* mutants producing indehiscent fruits were also carried out. Besides obtaining additional alleles of SHP1 and SHP2 through EMS mutagenesis of shp2-1 and shp1-1 seed stocks, indehiscent mutants that were not allelic to either SHP1 or SHP2, respectively were also obtained. Because the GT140 studies suggested the possibility that one or more of these indehiscent mutants might correspond to the IND1 gene, IND1 from several of these mutants was cloned and sequenced. Four alleles represent independent mutant alleles of IND1. The strongest allele, ind1-2, contains a single nucleotide deletion within codon 55 that results in a frameshift and production of a truncated protein of 64 rather than 198 amino acids. The ind1-1 and ind1-3 alleles contain nucleotide substitutions at codons 141 and 128 that changes a leucine amino acid to a phenylalanine and an arginine to a histidine, respectively. These affected amino acids are both at conserved positions within the bHLH domain. The ind1-4 allele contains a nucleotide substitution at codon 92 that changes a glutamine to a stop codon, causing production of a truncated protein of 91 amino acids. Since inactivation of this bHLH transcription factor prevents fruit dehiscence, the gene is referred to as INDEHISCENT1 (IND1) and the mutant as, ind1. To date, ind1 represents the only reported single gene mutation in *Arabidopsis* that specifically blocks fruit dehiscence.

To determine whether lignified margin cells are also affected by mutations in IND, we examined the lignification pattern of ind fruit compared to wild-type. While lignification of the vascular bundles and inner valve layer appear unaffected in ind fruit, we observed no lignified cells throughout the margins of ind-2 fruit. As margin lignification is only partially affected in shp fruit, and unaffected in alc fruit (Liljegren, S. J., et al. *Nature*, 404(6779):766–70 (2000), Rajani, S., and Sundaresan, V. *Curr. Biol.* 11: 1914–1922 (2001)), these results indicate that IND is primarily responsible for controlling the lignification of margin cells. Interestingly, the margins of ind-1 fruit, like alc fruit, are lignified, suggesting that the role of IND in separation zone specification is genetically distinct from its role(s) in margin constriction and lignification.

IND Regulates Expression of the YJ80 Margin Marker

To further monitor the effect of mutations in IND on cellular differentiation at the margin, expression of molecular markers derived from an enhancer trap screen (Eshed, Y., et al. *Cell* 99, 199–209 (1999)) was examined in ind fruit compared to wild-type. We discovered that the expression pattern of one marker, YJ80, is dramatically affected by mutations in IND. In wild-type fruit, YJ80 is expressed in stripes at the margin, in the guard cells scattered throughout the valves, and in the seed abscission zone. Mutations in IND completely disrupt expression of this marker throughout the margins, whereas the other fruit expression domains are unaffected.

Since we could detect differences between the margin defects of ind and shp1 shp2 fruit, and the phenotype of alc fruit is clearly distinct from that of ind and shp1 shp2, we expected that the phenotypes of these three mutants might be further distinguished with margin markers. Indeed, examination of the YJ80 marker in shp1 shp2 and alc fruit revealed that this marker is still present at the apical fruit margins of both mutants, although expression of the marker is disrupted at the basal margins of shp1 shp2 fruit, and at the central margins of alc fruit. These results correspond with our observations that apical margin development is more severely affected in ind fruit than in shp1 shp2 fruit, and further suggest that IND may be the key regulator of the gene corresponding to YJ80.

IND Encodes the GT140 bHLH Transcription Factor

Through our previous studies, we identified a margin-specific marker, GT140, that is largely absent from the margins of both shp1 shp2 and 35S::FUL indehiscent fruit (Sundaresan, *Genes Dev.* 9:1797–1810 (1995), Liljegren et al, supra, Ferrándiz, et al. *Science* 289, 436–438 (2000)). Since these results suggested that the gene corresponding to GT140 could be involved in margin development, we isolated genomic sequence flanking the Ds transposon using TAIL/PCR (Tsugeki, *Plant J.* 10, 479–489 (1996)). The insertion site was found to be on chromosome 4 between two predicted ORFs, At4g00120 and At4g00130. Subsequent analysis of At4g00120 demonstrated that a genomic fragment containing 2.6 kb from the promoter region directed expression of β-glucuronidase in the same margin-specific pattern as GT140. Furthermore, approximately 25% of the transgenic lines failed to show significant GUS activity and produced indehiscent fruit, suggesting that At4g00120 was co-suppressed in these lines and could be required for fruit dehiscence.

At4g00120, an open reading frame with no introns, encodes a protein with a basic helix-loop-helix (bHLH) domain. To investigate whether this gene might be affected by mutations at the ind locus, we sequenced the coding region in each of our mutant alleles. All five were found to contain single nucleotide changes within the coding region, and three, including ind-2, would cause production of a truncated protein without the bHLH domain. Complementation using a 3.4 kb genomic fragment spanning At4g00120 rescues the ind mutant phenotype, further confirming that IND is the GT140 bHLH factor.

Analysis of IND cDNA clones derived from 5' and 3' RACE-PCR suggests that the IND transcript is 751 nucleotides (nt), with a 510 nt open reading frame, and 5' and 3' untranslated regions of 40 and 201 nt, respectively.

IND Represents a Unique Class of Eukaryotic bHLH Proteins

Transcriptional regulators with a bHLH domain bind DNA through residues in the basic region while the helix-loop-helix domain promotes dimerization, allowing family members to form hetero- or homo-dimers (Murre, C., et al. Cell 56, 777–783 (1989)). Together, the two basic regions of the dimer usually recognize specific palindromic DNA hexamers with the consensus sequence CANNTG, such that each bHLH protein binds a half-site. Eukaryotic bHLH proteins have been classified into six major groups according to their DNA-binding specificity, the presence of additional characteristic domains, and phylogenetic analysis (Ledent, V., and Vervoort, M., Genome Res. 11, 754–770 (2001)). All previously characterized yeast and plant bHLH proteins have been assigned to the ancestral B-class, which bind to the CACGTG E-box (also known as the plant G-box).

Comparison of the bHLH domain of IND with those of other eukaryotic family members has shown that the basic region is atypical. All A- and B-class bHLH proteins contain a critical glutamic acid residue (E) at site 9 within the basic region. This particular residue has been shown to contact the outer CA nucleotides of the E-box and is required for DNA binding (Fisher, F., and Goding, C. R. (1992). EMBO J. 11, 4103–4109). In the basic region of IND and several other closely related plant sequences, an alanine residue (A) is present at site 9 instead of the glutamic acid. Although certain C-class bHLH-PAS proteins such as Single-minded (Sim) and Trachealess (Trh) also have atypical basic regions with alanines at this position, IND is not closely related to members of this class nor does it contain a predicted PAS domain (Nambu (1991) Cell 67:1157–1167; Wilk, R. (1996) Genes Dev. 10:93–102).

IND shares more than 60% sequence identity within the bHLH domain with at least twenty-seven other predicted plant bHLH proteins with atypical basic regions. However, sequence conservation between IND and the five closest Arabidopsis relatives is primarily restricted to the bHLH domain. For instance, the most related sequence, At5g09750, shares 82% identity with IND in the bHLH domain, but only 35% elsewhere.

ALC, which is also required for fruit dehiscence, shares only 42% identity with IND in the bHLH domain, and, like most Arabidopsis bHLH family members, shows characteristics of the B-class basic domain (Rajani, supra; Buck, M. J., and Atchley, W. R. J. Mol. Evol. 56, 742–750 (2003)). The similarity between the alc-1, alc-2, and ind-1 mutant phenotypes is intriguing, as alc-1 is predicted to be a null allele (Rajani, supra), but ind-1 is not. Molecular analysis has revealed that the ind-1 mutation would result in substitution of a phenylalanine for a leucine within the first helix of the bHLH domain. This particular residue is observed in >98% of all known eukaryotic bHLH proteins, and has been shown from structural studies of the Max homodimer to pack together with other conserved hydrophobic amino acids in the second helix and stabilize the intramolecular interactions of the four-helix bundle (Ferré-D'Amaré, et al. Nature 363:38–45 (1993); Atchley, W. R., et al. J. Mol. Evol. 48:501–516 (1999); Atchley, et al. Mol. Biol. Evol. 17:164–178 (2000)). Substitution of another hydrophobic residue at this position, although conservative, appears to significantly reduce activity of the ind-1 protein.

In contrast to ind-1, replacement of an arginine with a histidine in the basic region of the ind-3 allele, results in a phenotype indistinguishable from that of the ind-2 allele. As this arginine is one of several residues known to make specific phosphate contacts within the DNA consensus sequence (Ferré-D'Amaré, et al. Nature 363:38–45 (1993); Ma, et al. Cell 77:451–459 (1993)), these results suggest that disruption of DNA binding is enough to abolish IND function entirely.

Expression of IND Expands Throughout the Valves of Ful Fruit

To determine the pattern of IND expression in wild-type and mutant fruit, we performed antisense in situ hybridization with an IND-specific probe. After fertilization, IND is expressed in stripes about four cells wide at the margins of developing wild-type fruit. We also detected IND expression in the only valve layer which becomes lignified later in fruit development, and in the vascular bundles of the replum. Like SHP1 and SHP2 (Ferrándiz, et al. Science 289:436–438 (1999)), expression of IND expands throughout the valves of ful mutant fruit, indicating that FUL is required to restrict IND expression at the margin from the valves.

Expanded IND Activity in Ful Fruit Inhibits Growth and Causes Ectopic Lignification Mutations in FUL cause severe defects in fruit growth, primarily due to lack of valve cell expansion after fertilization of the gynoecium (Gu, Q., et al. Development 125: 1509–1517 (1998)). Previously, we have found that the ectopic expression of SHP1 and SHP2 in ful fruit does not account for their reduced growth, as shp1 shp2 ful fruit are not significantly longer than ful fruit (Ferrándiz, et al. Science 289:436–438 (1999)). To determine whether ectopic IND activity could instead be primarily responsible for the expansion defects of ful fruit, we constructed the ind ful double mutant. Remarkably, we discovered that fruit growth is considerably restored in ind ful fruit compared to ful fruit. Whereas mature ful fruit (2.5+/−0.2 mm) are 25% the length of wild-type fruit (10.1+/−0.7), ind ful fruit (6.8+/−0.4) are significantly longer—more than twice the length of ful fruit and 67% the length of wild-type. Scanning electron micrographs of ful and ind ful fruit compared to wild-type demonstrate the restoration of valve epidermal cell expansion due to loss of IND activity. Furthermore, differentiation of some epidermal cells into guard cells is seen in ind ful fruit, and is never observed in ful fruit.

In addition to growth defects, ful fruit also show ectopic lignification of several valve cell layers (Ferrándiz, et al. Science 289:436–438 (1999)). During wild-type fruit development, lignification of a single inner valve cell layer is thought to contribute to fruit opening. In ful fruit, lignification of three additional valve layers occurs. Because we found that IND is required for lignification of the wild-type fruit margin, we expected that expanded IND activity might result in the ectopic lignification of ful fruit. Indeed, as lignification of only the inner valve layer is observed in ind ful fruit, expanded IND activity is not only largely responsible for the lack of valve expansion, but also causes the ectopic valve lignification of ful fruit.

Since SHP1, SHP2, and IND are each expressed at the margins of wild-type fruit, we have interpreted their expression throughout the valves of ful fruit as suggestive of an expansion of margin identity (Ferrándiz, et al. Science 289:436–438 (1999); this work). The notable suppression of the ful fruit phenotype conveyed by loss of IND activity provides experimental validation of this hypothesis, and further supports a link between the role of IND in promoting decreased cell expansion at the margin during fruit growth and its role in directing the later lignification of a subset of margin cells. Furthermore, the phenotypic differences between ind ful and shp1 shp2 ful fruit constitute compelling genetic evidence that IND expression and/or activity is not simply regulated by SHP1 and SHP2.

An interesting lead to follow in the search for additional factors which inhibit margin cell expansion, or promote their subsequent lignification, is YJ80. Like IND, expression of the YJ80 marker at the margin expands throughout the valves of ful fruit, and, with the exception of the few guard cells, is completely absent in the valves of ind ful fruit. As expected from analysis of YJ80 in shp1 shp2 and alc fruit, expression of YJ80 persists throughout the valves of shp1 shp2 ful and alc ful fruit, strongly suggesting that the gene corresponding to this marker is specifically regulated by IND.

Plants with Ectopic IND Expression Produce Ful-Like Fruit

To further explore the developmental effects of ectopic IND activity, we generated transgenic plants expressing IND under control of either the constitutive cauliflower mosaic virus 35S promotor or the FUL promoter, which directs expression in the inflorescence meristem, cauline leaves, and throughout the developing valves of the gynoecium. Phenotypic analysis revealed that 17 of 101 35S::IND and 48 of 135 FUL::IND T1 plants produced ful-like fruit with severe growth defects. Furthermore, a significant number of 35S::IND and FUL::IND T1 plants exhibited weaker ful-like fruit phenotypes, much like the fruit produced by plants constitutively expressing SHP1 and SHP2. These results correspond well with our discovery that mutations in IND significantly suppress the ful fruit phenotype, and demonstrate that ectopic IND activity is sufficient to inhibit fruit growth.

Loss of IND, SHP, and ALC Activity Largely Suppresses the Ful Fruit Phenotype

Since mutations in IND not only have the most severe effect on margin development, but also suppress the ful phenotype more dramatically than mutations in ALC, or SHP1 and SHP2, we wondered if these transcription factors regulate any aspects of margin development independently of IND. To address this question, we have conducted systematic genetic analysis to uncover the relative contributions of IND, SHP1, SHP2, and ALC to margin development and to determine the extent their ectopic activities have on the ful fruit phenotype.

By comparing ind shp1 shp2, ind alc, and ind fruit, we observed an enhanced loss apical margin definition in ind shp1 shp2 fruit compared to ind fruit, but did not detect any morphological differences between ind alc and ind fruit. A smaller, but similar loss of margin definition was also evident in our examination of shp1 shp2 alc fruit compared to shp1 shp2 fruit. These results suggest that SHP1 and SHP2 do regulate some aspects of margin development independently of IND and ALC, and that ALC activity is primarily encompassed by IND.

The IND-independent activity of SHP1 and SHP2 is much more apparent when comparing ind shp1 shp2 ful to ind ful fruit. Fruit length in ind shp1 shp2 ful fruit (8.5+/−0.8 mm) is largely restored (84%) to wild-type, and the overall appearance of the fruit, while rumpled, is more like wild-type, due to increased lateral valve cell expansion. Furthermore, scanning electron micrographs of ind shp1 shp2 ful fruit compared to wild-type, ful and ind ful fruit demonstrate the extensive restoration of guard cell differentiation due to loss of ectopic IND, SHP 1, and SHP2 activity. Support for the ALC-independent activity of SHP1 and SHP2 is also more evident in comparing shp1 shp2 alc ful to alc ful fruit. Although the fruit length (5.1+/−0.4 mm) of shp1 shp2 alc ful fruit is only partially restored (51%) compared to wild-type, it is significantly longer than that of alc ful fruit (4.0+/−0.3 mm). Taken together, these results clearly indicate that SHP1 and SHP2 regulate factors involved in margin development and cell expansion independently of IND and ALC.

Although our initial observations of ind alc fruit suggested that ALC might not play any roles in margin development independent of ND, analysis of ind alc ful and ind alc shp1 shp2 ful fruit has revealed that ALC does possess both IND- and SHP-independent roles. Fruit produced by the ind alc ful mutant are significantly longer (8.2+/−0.6 mm) than ind ful fruit (6.8+/−0.4 mm). Furthermore, while not significant, a slight increase in length is also observed in comparing ind shp1 shp2 ful (8.5+/−0.8 mm) to ind alc shp1 shp2 ful (9.1+/−0.9 mm) fruit.

IND, SHP, ALC, and FUL Activities Contribute to Differentiation of the Lignified Valve Layer In addition to finding that SHP and ALC have ND-independent roles in margin development, we also discovered that together with IND and FUL these factors are involved in specifying lignification of the lignified valve layer. Examination of ind alc shp1 shp2 fruit compared to wild type revealed that a few cells in the lignified valve layer adjacent to each valve margin fail to lignify. A similar, but less penetrant, retraction of lignified valve layer cells from the replum was also observed in ind shp1 shp2 fruit. The appearance and size of these non-lignified cells is most like those found in the neighboring mesophyll cell layers.

In wild-type fruit, FUL is expressed throughout the valves (Gu et al., 1998). Previously we have found that the expression of FUL retracts slightly from the valve margin in shp1 shp2 mutant fruit (Ferrándiz et al., 2000b). In ind mutants, we also observe a slight retraction of the FUL from the margin. The retraction of FUL from the margin is more dramatic in ind alc shp1 shp2 quadruple mutant fruit, and correlates with the absence of lignified cells near the margin in the lignified valve layer. When FUL activity is removed in the ind alc shp1 shp2 ful quintuple mutant, lignification of the lignified valve layer is completely absent except for a few cells at the base of the fruit. The observation that lignification of this layer is reduced but not eliminated in ind shp1 shp2 ful quadruple mutant fruit (data not shown) indicates that ALC also plays a role in specifying this cell type. Since the lignified valve layer is completely eliminated only when all five transcription factors—IND, ALC, SHP 1, SHP2, and FUL—are inactivated, it is evident that each factor contributes to lignification of this layer.

Experimental Procedures

Plants

Mutant alleles of IND and ALC were obtained through ethyl methanesulphonate mutagenesis as previously described (Liljegren, Nature 404:766–770 (2000)). The ind-2 allele contains a single nucleotide deletion within codon 26, which results in a frameshift and production of a truncated protein of 35 amino acids. The ind-1 and ind-3 alleles contain nucleotide substitutions within codons 112 and 99, which change a leucine to a phenylalanine and an arginine to a histidine, respectively. The ind-4 and ind-5 alleles contains nucleotide substitutions within codons 63 and 13, which change a glutamine and a tryptophan to stop codons, causing production of truncated proteins of 62 and 12 amino acids, respectively. The alc-2 mutation contains a nucleotide substitution at the splice donor site of the third intron, which should disrupt splicing of the transcript region encoding the second helix of the bHLH domain. The ind-2 and alc-2 alleles were backcrossed three times to Ler and used for subsequent genetic analyses, along with the shp1-1, shp2-1, and ful-5 alleles.

Plants homozygous for the ind-2 and/or alc-2 alleles were detected with CAPS (cleaved amplified polymorphic sequence) markers based on an AluI site abolished by the ind-2 mutation and an AseI site introduced by the alc-2 mutation. The shp1-1 and shp2-1 mutations were detected as described previously.

cDNA Analysis

To examine the transcripts produced at the IND locus, 5' and 3' RACE-PCR (Roche) were performed as described by the manufacturer using total or polyA RNA, respectively, as template. For 5' RACE, 5'-GAGTTGTGGTAATAA-CAAAGGTAAG-3' (SEQ ID NO:21) was used in the reverse transcriptase reaction, and additional nested oligos 5'-GGCTTCGTCGAGCATGGAAGC-3' (SEQ ID NO:22) and 5'-GAGCAACCACCGTCTGAGGATCG-3' (SEQ ID NO:23) were used in subsequent rounds of PCR. For 3' RACE, oligo dT was used in the reverse transcriptase reaction, and the nested primer 5'-CCCTGCCACGGTC-CCTAAGC-3' (SEQ ID NO:24) in a subsequent round of PCR. The resulting fragments were cloned into pCR2.1 (Invitrogen) and sequenced. Analysis of IND cDNA clones derived from 5' and 3' RACE-PCR suggests that the IND transcript is 751 nucleotides (nt), with a 510 nt open reading frame, and 5' and 3' untranslated regions of 40 and 201 nt, respectively. Further support for the assigned open reading frame is provided by an IND EST (AF488578).

Marker Analyses

To isolate flanking sequence from the GT140 marker (Sundaresan, et al. (1995) *Genes Dev.* 9:1797–1810), TAIL (Thermal Asymmetric Interlaced)/PCR was performed using nested oligos specific for the left and right transposon borders and degenerate primers as described previously (Tsugeki, et al. (1996) *Plant J.* 10:479–489). The transposon insertion was detected 2782 nucleotides 5' of the predicted ATG of At4g00120, and creates a duplication of 8 bp (GTATTTGC) flanking the insertion site.

The YJ80 enhancer trap line was generated by *Agrobacterium*-mediated transformation with the plasmid pOCA-28-15-991. Transgenic plants containing YJ80, GT140, YJ36 or a FUL marker were crossed into mutant plants. For β-glucuronidase expression analyses, fruit from wild-type and mutant plants were fixed, sectioned and stained with minor modifications.

Generation of Transgenic Plants

Using genomic DNA from the GT140 insertion line as a template, a 2.9 kb region spanning from 180 nucleotides upstream of the predicted At4g00120 translational start site and extending into the Ds insertion element was PCR amplified. This fragment was cloned into pCR2.1 (Invitrogen), then excised as a SalI/BamHI fragment and cloned into the plant transformation vector, pBI101.3. 17 of 38 transgenic T1 lines produced indehiscent fruit.

A 3.4 kb genomic region of IND, extending 2740 bases 5' and 480 bases 3' of the coding region, was PCR amplified using Columbia DNA as a template. This fragment was cloned into pCR2.1, then excised as an XbaI fragment and cloned into the pEL112 plant transformation vector. Basta-resistant transgenic plants exhibiting a complemented phenotype were PCR analyzed to confirm that they were homozygous for the ind-2 allele.

A full-length IND cDNA was PCR amplified with the oligos (5'-CGTCGACGATGAAAATGGAAAATGGTAT-GTATA-3' (SEQ ID NO:25) and 5'-CGGATCCGTTCAT-CAGGGTTGGGAGTTGTG-3') (SEQ ID NO:26) using Columbia DNA as a template. After cloning this product into pCR2.1, a SalI/BamHI fragment containing the IND cDNA was cloned into the pBTN-JIT vector. The resulting construct placed IND under the control of a tandem repeat of the 355 promoter.

Microscopy and Histology

Wild-type (Landsberg *erecta* ecotype), mutant, and transgenic fruit and flowers were fixed, prepared, and analyzed by scanning electron microscopy as previously described. Tissue fixation and phloroglucinol staining of paraplast sections (8 or 10 µm) from late stage 17 fruit were done as described (Liljegren et al., 2000). Plastic sections (3 µm) were prepared with JB4 resin (Electron Microscopy Sciences) as described (Roeder et al., 2003) from the tenth stage 17 fruit on wild-type and mutant inflorescences.

In Situ Hybridization

Wild type and mutant sections were hybridized with antisense or sense RNA as described. The IND probe was synthesized with T7 RNA polymerase from a SalI-digested pINDAS template to generate a 328 nucleotide antisense transcript encompassing the 5' region through part of the first helix of the bHLH domain. pINDAS was created by ligating the IND product PCR amplified from Colombia DNA with 5'-GAGCAACCACCGTCTGAGGATCG-3' (SEQ ID NO:27) and 5'-CGTCGACGATGAAAATGGAAAATGG-TATGTATA-3' (SEQ ID NO:28) into the pCR2.1 vector.

Example 2

Two IND1 orthologs were isolated from *Brassica napus* plants. Since *Brassica napus* has an allotetraploid genome, it is not surprising that two different IND1 orthologs are present in the genome. The two sequences are designated Bn IND1 and Bn IND2. An alignment of the amino acid sequences of Bn IND1 and Bn IND2 with SEQ ID NO:13 are depicted in FIG. 1. An alignment of the nucleotide sequences of Bn IND1 and Bn IND2 with SEQ ID NO:14 are depicted in FIG. 2. The amino acid sequence of Bn IND1 is approximately 63% identical to SEQ ID NO:2 of the present invention, as measured with BLAST without the low complexity filter. The amino acid sequence of Bn IND2 is approximately 67% identical to SEQ ID NO:2 of the present invention. Like the *Arabidopsis* IND 1 sequence, the *Brassica* IND sequences include an alanine residue (A) at site 9 of the basic region instead of the glutamic acid (e.g., position 139 of SEQ ID NO:9 and position 112 of SEQ ID NO:10).

Transformation of either Bn IND1 or Bn IND2 into ind1 mutant *Arabidopsis* plants resulted in complementation of the mutant phenotype. These results demonstrate that Bn IND1 and Bn IND2 carry out the same basic functions as IND1.

Example 3

Figure 3:
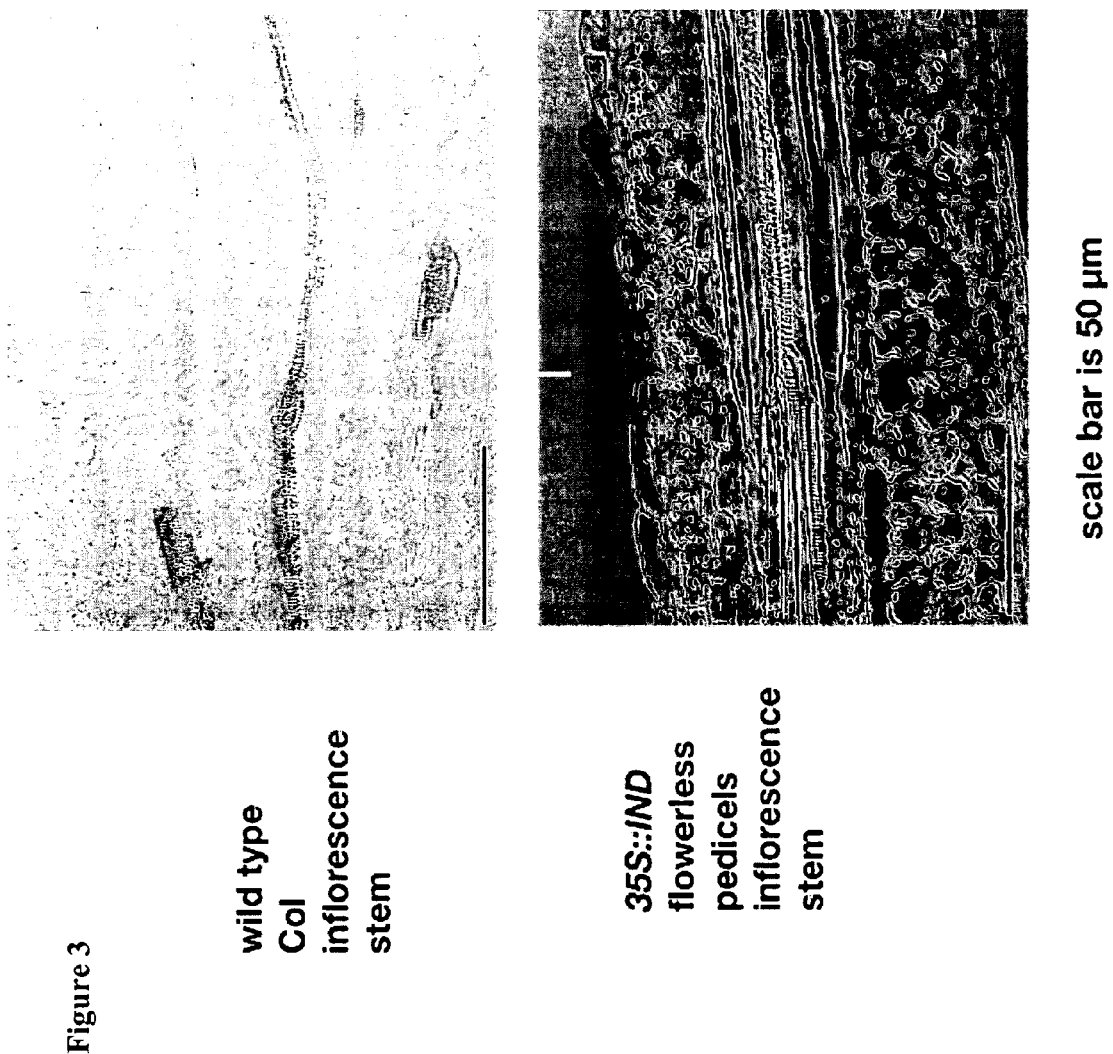
FIG. 3 depicts lignification of wildtype and 35S:IND1 transgenic *Arabidopsis* stems.

To examine the effect of ectopic expression of IND1 on lignification, we introduced a 35S::IND1 construct into *Arabidopsis* plants and assayed for lignification. Upon germination, *Arabidopsis* plants produce a rosette of leaves on the surface of the soil. These leaves are closely spaced as a result of the lack of internode elongation between leaves. Upon the transition to reproductive development in *Arabi*- dopsis, the main stem is often referred to as the inflorescence stem, since it is responsible for producing flowers on its flanks. This stem elongates considerably, giving the plant its characteristic height. Inspection of the lignification patterns in the inflorescence stem of wild-type plants, determined by the lignin-specific phloroglucinol stain of a stem section, revealed the normal pattern of stem lignification in the tracheary elements. A similar stem section from 35S::IND1 plant stems appeared to reveal ectopic lignification. These results are depicted in FIG. 3. The two images in the figure were taken under the same magnification. The 35S::IND1 plants are appear to be more extensively lignified than are wild-type plants, indicating that the ectopic expression of IND1 in the stem is sufficient to promote ectopic lignification of stem cells.

This application is related to U.S. application Ser. No. 09/349,677, filed Jul. 8, 1999, which is a divisional application of U.S. application Ser. No. 09/067,800, filed Apr. 28, 1998, which claims the benefit of priority of U.S. Provisional Application No. 60/051,030, filed Jun. 27, 1997, each of which is incorporated by reference in its entirety.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An expression cassette comprising a heterologous promoter operably linked to a polynucleotide, or a complement thereof, wherein the polynucleotide encodes a polypeptide that is at least 60% identical to SEQ ID NO:2, wherein the polypeptide comprises a basic helix-loop-helix domain, and complements an *Arabidopsis ind*1 mutant phenotype when introduced into an *Araidopsis ind*1 mutant plant.

2. The expression cassette of claim 1, wherein the polynucleotide comprises nucleotides 2765–3361 of SEQ ID NO: 1.

3. The expression cassette of claim 1, wherein the promoter is constitutive.

4. The expression cassette of claim 1, wherein the promoter is tissue specific.

5. The expression cassette of claim 4, wherein the promoter is a dehiscence zone specific promoter.

6. A plant comprising a recombinant expression cassette, the expression cassette comprising a promoter operably linked to a polynucleotide, or a complement thereof, wherein the polynucleotide encodes a polypeptide that is at least 60% identical to SEQ ID NO:2, wherein the polypeptide comprises a basic helix-loop-helix domain, and complements an *Arabidopsis ind*1 mutant phenotype when introduced into an *Araidopsis ind*1 mutant plant.

7. The plant of claim 6, wherein the polynucleotide comprises nucleotides 2765–3361 of SEQ ID NO:1.

8. The plant of claim 6, wherein the polynucleotide is at least 60% identical to a nucleotide sequence encoding SEQ ID NO:2.

9. The plant of claim 6, wherein the polynucleotide is operably linked to the promoter in the antisense orientation.

10. The plant of claim 6, wherein the polynucleotide is operably linked to the promoter in the sense orientation.

11. The plant of claim 10, wherein the plant further comprises a second polynucleotide encoding a second polypeptide that is at least 60% identical to SEQ ID NO:2, wherein the polypeptide comprises a basic helix-loop-helix domain, and complements an *Arabidopsis ind*1 mutant phenotype when introduced into an *Araidopsis ind*1 mutant plant, wherein the second polynucleotide is operably linked to a second promoter in the antisense orientation.

12. The plant of claim 6, wherein lignification is reduced in valve margin cells of the plant.

13. The plant of claim 6, wherein lignification is enhanced in the plant.

14. The plant of claim 6, wherein the promoter is a dehiscence zone-selective regulatory element.

15. The plant of claim 14, wherein the promoter is constitutive.

16. The plant of claim 6, wherein the plant is a *Brassica* species.

17. The plant of claim 6, wherein the plant is characterized by delayed seed dehiscence compared to a plant not comprising the expression cassette.

18. A method of delaying fruit dehiscence in a plant, the method comprising the steps of,
  (a) treating seeds or plants with a chemical mutagen or ionizing radiation;
  (b) identifying plants in which the expression of a polypeptide at least 60% identical to SEQ ID NO:2 is suppressed, wherein the polypeptide comprises a basic helix-loop-helix domain, and complements an *Arabidopsis ind*1 mutant phenotype when introduced into an *Araidopsis ind*1 mutant plant; and
  (c) selecting a plant with delayed fruit dehiscence compared to a plant in which the expression of the polypeptide is not suppressed.

19. The method of claim 18, wherein the plant selected in step (c) comprises a mutated IND1 gene.

20. A method of selecting a plant with delayed fruit dehiscence, the method comprising the steps of,
  (a) introducing into plants a recombinant expression cassette comprising a promoter operably linked to a polynucleotide, or a complement thereof, wherein the polynucleotide is at least 60% identical to a nucleotide sequence encoding SEQ ID NO:2;
  (b) identifying plants in which the expression of a polypeptide at least 60% identical to SEQ ID NO:2 is suppressed, wherein the polypeptide comprises a basic helix-loop-helix domain and complements an *Arabidopsis ind*1 mutant phenotype when introduced into an *Araidopsis ind*1 mutant plant; and
  (c) selecting a plant with delayed fruit dehiscence compared to a plant in which the expression of the polypeptide is not suppressed.

21. The method of claim 20, wherein the nucleotide sequence is nucleotides 2765–3361 of SEQ ID NO:1.

22. The method of claim 20, wherein the polynucleotide is operably linked to the promoter in the antisense orientation.

23. The method of claim 20, wherein the polynucleotide is operably linked to the promoter in the sense orientation.

24. The method of claim 23, wherein the polynucleotide further comprises a second polynucleotide at least 60% identical to a nucleotide sequence encoding SEQ ID NO:2, wherein the second polynucleotide is operably linked to a second promoter in the antisense orientation.

25. The method of claim 20, wherein lignification is reduced in valve margin cells.

26. The method of claim 20, wherein the promoter is a dehiscence zone-selective regulatory element.

27. The method of claim 20, wherein the recombinant expression cassette is introduced into the plant using *Agrobacterium*.

28. The method of claim 20, wherein the plant is a *Brassica* species.

* * * * *